(12) United States Patent
Zachar

(10) Patent No.: US 10,500,360 B1
(45) Date of Patent: Dec. 10, 2019

(54) CATHETER FOR CLEANING OF TRACHEAL VENTILATION TUBES

(71) Applicant: TELEFLEX LIFE SCIENCES UNLIMITED COMPANY, Hamilton (BM)

(72) Inventor: Oron Zachar, Tel Aviv (IL)

(73) Assignee: TELEFLEX LIFE SCIENCES UNLIMITED COMPANY, Hamilton (BM)

( * ) Notice: Subject to any disclaimer, the term of this patent is extended or adjusted under 35 U.S.C. 154(b) by 1006 days.

(21) Appl. No.: 14/821,828

(22) Filed: Aug. 10, 2015

Related U.S. Application Data

(60) Provisional application No. 62/043,428, filed on Aug. 29, 2014.

(51) Int. Cl.
*A61M 16/04* (2006.01)
*A61M 25/10* (2013.01)
*A61B 90/70* (2016.01)

(52) U.S. Cl.
CPC ......... *A61M 16/0463* (2013.01); *A61B 90/70* (2016.02); *A61M 25/10* (2013.01); *A61B 2090/701* (2016.02)

(58) Field of Classification Search
CPC .. A61M 25/10; A61M 39/00; A61M 16/0463; A61M 2209/10; A61M 2025/0019; A61M 16/0816; A61M 16/0404; A61M 16/0475; A61M 16/0486; A61B 2090/701
See application file for complete search history.

(56) References Cited

U.S. PATENT DOCUMENTS 3,211,150 A  10/1965  Foderick
3,502,069 A   3/1970  Silverman
(Continued)

FOREIGN PATENT DOCUMENTS

EP  0692273 A1  1/1996
EP  1239907 B1  9/2007
(Continued)

OTHER PUBLICATIONS

Dwyer Instruments; Gage Fluid web page; https://web-beta.archive.org/web/20160306163019/http://www.dwyer-inst.com/Product/Miscella neous/Accessories/GageFluids/GageFluids; Mar. 6, 2016 [downloaded from world wide web May 27, 2017].
(Continued)

*Primary Examiner* — Timothy A Stanis
*Assistant Examiner* — Cana A Gallegos
(74) *Attorney, Agent, or Firm* — Baker & Hostetler LLP

(57) ABSTRACT

In embodiments of the present invention, a suction cleaning system component is provided for use in cleaning an interior of a tracheal ventilation tube when the suction cleaning system component is connected to the tracheal ventilation tube and a ventilator. Typically, the suction cleaning system component is used in a closed endotracheal suction system environment. The suction cleaning system component comprises a cleaning catheter and a manifold. The manifold comprises an obstruction element, which is moveable with respect to (i) the ventilator port and (ii) the expandable element. The obstruction element is configured to assume a plurality of states, including an obstruction state.

19 Claims, 13 Drawing Sheets

(56) References Cited

U.S. PATENT DOCUMENTS

| | | |
|---|---|---|
| 3,671,979 A | 6/1972 | Moulopoulos |
| 3,780,736 A | 12/1973 | Chen |
| 3,985,141 A | 10/1976 | Stanley et al. |
| 4,016,885 A | 4/1977 | Bruner |
| 4,064,882 A | 12/1977 | Johnson et al. |
| 4,134,407 A | 1/1979 | Elam |
| 4,159,722 A | 7/1979 | Walker |
| 4,166,468 A | 9/1979 | Haynie |
| 4,182,344 A | 1/1980 | Benson |
| 4,240,433 A | 12/1980 | Bordow |
| 4,245,639 A | 1/1981 | La Rosa |
| 4,324,262 A | 4/1982 | Hall |
| 4,351,328 A | 9/1982 | Bodai |
| 4,469,100 A | 9/1984 | Hardwick |
| 4,501,273 A | 2/1985 | McGinnis |
| 4,510,933 A | 4/1985 | Wendt et al. |
| 4,555,242 A | 11/1985 | Saudagar |
| 4,569,344 A | 2/1986 | Palmer |
| 4,583,917 A | 4/1986 | Shah |
| 4,606,347 A | 8/1986 | Fogarty et al. |
| 4,607,635 A | 8/1986 | Heyden |
| 4,630,606 A | 12/1986 | Weerda et al. |
| 4,638,539 A | 1/1987 | Palmer |
| 4,649,914 A | 3/1987 | Kowalewski |
| 4,691,702 A | 9/1987 | Chantzis |
| 4,758,223 A | 7/1988 | Rydell |
| 4,762,125 A | 8/1988 | Leiman et al. |
| 4,805,611 A | 2/1989 | Hodgkins |
| 4,813,935 A | 3/1989 | Haber et al. |
| 4,850,982 A | 7/1989 | Erlich et al. |
| 4,886,496 A | 12/1989 | Conoscenti et al. |
| 4,932,959 A | 6/1990 | Horzewski et al. |
| 4,946,440 A | 8/1990 | Hall |
| 4,961,738 A | 10/1990 | Mackin |
| 5,003,657 A | 4/1991 | Boiteau et al. |
| 5,029,580 A | 7/1991 | Radford et al. |
| 5,067,497 A | 11/1991 | Greear et al. |
| 5,073,164 A | 12/1991 | Hollister et al. |
| 5,098,384 A | 3/1992 | Abrams |
| 5,101,817 A | 4/1992 | Etter |
| 5,125,893 A | 6/1992 | Dryden |
| 5,134,996 A | 8/1992 | Bell |
| 5,139,018 A | 8/1992 | Brodsky et al. |
| 5,181,908 A | 1/1993 | Bell |
| 5,188,618 A | 2/1993 | Thomas |
| 5,215,522 A | 6/1993 | Page et al. |
| 5,218,970 A | 6/1993 | Turnbull et al. |
| 5,254,098 A | 10/1993 | Ulrich et al. |
| 5,269,756 A | 12/1993 | Dryden |
| 5,277,177 A | 1/1994 | Page et al. |
| 5,279,549 A | 1/1994 | Ranford |
| 5,309,902 A | 5/1994 | Kee et al. |
| 5,325,851 A | 7/1994 | Reynolds et al. |
| 5,336,172 A | 8/1994 | Bales et al. |
| 5,337,730 A | 8/1994 | Maguire |
| 5,349,950 A | 9/1994 | Ulrich et al. |
| 5,360,403 A | 11/1994 | Mische |
| 5,361,753 A | 11/1994 | Pothmann et al. |
| 5,364,345 A | 11/1994 | Lowery et al. |
| 5,364,358 A | 11/1994 | Hewitt et al. |
| 5,460,613 A | 10/1995 | Ulrich et al. |
| 5,487,383 A | 1/1996 | Levinson |
| 5,490,503 A | 2/1996 | Hollister |
| 5,545,179 A | 8/1996 | Williamson, IV |
| 5,582,161 A | 12/1996 | Kee |
| 5,611,336 A | 3/1997 | Page et al. |
| 5,634,937 A | 6/1997 | Mollenauer et al. |
| 5,694,922 A | 12/1997 | Palmer |
| 5,709,691 A | 1/1998 | Morejon |
| 5,715,815 A | 2/1998 | Lorenzen et al. |
| 5,730,123 A | 3/1998 | Lorenzen et al. |
| 5,738,091 A | 4/1998 | Kee et al. |
| 5,743,258 A | 4/1998 | Sato et al. |
| 5,775,325 A | 7/1998 | Russo |
| 5,779,687 A | 7/1998 | Bell et al. |
| 5,832,920 A | 11/1998 | Field |
| 6,045,531 A | 4/2000 | Davis |
| 6,082,361 A | 7/2000 | Morejon |
| 6,227,200 B1 | 5/2001 | Crump et al. |
| 6,270,489 B1 | 8/2001 | Wise et al. |
| 6,318,368 B1 | 11/2001 | Morejon |
| 6,494,208 B1 | 12/2002 | Morejon |
| 6,602,219 B2 | 8/2003 | Madsen et al. |
| 6,612,304 B1 | 9/2003 | Cise et al. |
| 6,647,984 B1 | 11/2003 | O'Dea |
| 6,679,262 B1 | 1/2004 | Morejon |
| 6,805,125 B1 | 10/2004 | Crump et al. |
| 6,918,893 B2 | 7/2005 | Houde et al. |
| 6,923,184 B1 | 8/2005 | Russo |
| 6,932,788 B2 | 8/2005 | Kamiyama et al. |
| 6,935,339 B2 | 8/2005 | Mattar Neto et al. |
| 6,976,974 B2 | 12/2005 | Houde et al. |
| 7,021,313 B1 | 4/2006 | Crump et al. |
| 7,051,737 B2 | 5/2006 | Kolobow et al. |
| 7,060,135 B2 | 6/2006 | Morejon |
| 7,156,827 B2 | 1/2007 | McNary et al. |
| 7,172,572 B2 | 2/2007 | Diamond et al. |
| 7,179,272 B2 | 2/2007 | Kieturakis et al. |
| 7,188,623 B2 | 3/2007 | Anderson et al. |
| 7,191,782 B2 | 3/2007 | Madsen |
| 7,204,252 B2 | 4/2007 | Johnson |
| 7,273,473 B2 | 9/2007 | Owens et al. |
| 7,278,429 B2 | 10/2007 | Johnson |
| 7,383,736 B2 | 6/2008 | Esnouf |
| 7,478,636 B2 | 1/2009 | Madsen et al. |
| 7,556,041 B2 | 7/2009 | Madsen |
| 7,625,207 B2 | 12/2009 | Hershey et al. |
| 7,669,600 B2 | 3/2010 | Morejon |
| 7,717,116 B2 | 5/2010 | Mijers |
| 7,726,315 B2 | 6/2010 | Field |
| 7,775,206 B2 | 8/2010 | Anderson et al. |
| 7,789,893 B2 | 9/2010 | Drasler et al. |
| 7,819,890 B2 | 10/2010 | Russo et al. |
| 7,854,728 B2 | 12/2010 | Boyle, Jr. |
| 7,878,202 B2 | 2/2011 | Anderson et al. |
| 7,967,811 B2 | 6/2011 | Kumar |
| 8,002,732 B2 | 8/2011 | Visconti |
| 8,133,326 B2 | 3/2012 | Bracken |
| 8,157,919 B2 | 4/2012 | Vazales et al. |
| 8,210,168 B2 | 7/2012 | Swisher |
| 8,215,306 B2 | 7/2012 | Brewer et al. |
| RE43,886 E | 1/2013 | Mijers |
| 8,381,345 B2 | 2/2013 | Vazales et al. |
| 8,382,908 B2 | 2/2013 | Vazales et al. |
| 8,397,577 B2 | 3/2013 | Slocum, Sr. et al. |
| 8,414,544 B2 | 4/2013 | Resca |
| 8,434,488 B2 | 5/2013 | Li et al. |
| 8,458,844 B2 | 6/2013 | Vazales et al. |
| 8,468,637 B2 | 6/2013 | Vazales et al. |
| 8,486,100 B2 | 7/2013 | Oishi et al. |
| 8,534,287 B2 | 9/2013 | Vazales et al. |
| 8,556,851 B2 | 10/2013 | Hirszowicz et al. |
| 8,557,054 B2 | 10/2013 | Morejon |
| 8,601,633 B2 | 12/2013 | Vazales et al. |
| 8,631,798 B2 | 1/2014 | Varga et al. |
| 8,783,255 B2 | 7/2014 | Maguire et al. |
| 8,999,074 B2 | 4/2015 | Zachar et al. |
| 9,010,322 B2 | 4/2015 | Swisher |
| 9,095,286 B2 | 8/2015 | Vazales et al. |
| 9,119,926 B2 | 9/2015 | Cuevas et al. |
| 9,131,988 B2 | 9/2015 | Bagwell et al. |
| 9,220,859 B2 | 12/2015 | Li et al. |
| 9,248,249 B2 | 2/2016 | Li et al. |
| 9,332,891 B2 | 5/2016 | Vazales et al. |
| 9,352,112 B2 | 5/2016 | Sederstrom et al. |
| 9,386,907 B2 | 7/2016 | Vazales et al. |
| 9,398,837 B2 | 7/2016 | Vazales et al. |
| 9,480,537 B2 | 11/2016 | Stadelman et al. |
| 2003/0145860 A1 | 8/2003 | Johnson |
| 2003/0188749 A1 | 10/2003 | Nichols et al. |
| 2003/0209258 A1 | 11/2003 | Morejon |
| 2003/0216698 A1 | 11/2003 | McNary et al. |
| 2004/0082923 A1 | 4/2004 | Field |
| 2004/0221851 A1 | 11/2004 | Madsen |

(56) References Cited

U.S. PATENT DOCUMENTS

| | | |
|---|---|---|
| 2004/0221852 A1 | 11/2004 | Madsen |
| 2005/0172971 A1 | 8/2005 | Kolobow et al. |
| 2005/0279359 A1 | 12/2005 | LeBlanc et al. |
| 2006/0005841 A1 | 1/2006 | Anderson et al. |
| 2006/0099434 A1 | 5/2006 | Hoetger |
| 2006/0130847 A1 | 6/2006 | Morejon |
| 2006/0150981 A1 | 7/2006 | Johnson |
| 2006/0207605 A1 | 9/2006 | Anderson et al. |
| 2006/0278235 A1 | 12/2006 | White et al. |
| 2007/0021651 A1 | 1/2007 | Gobel |
| 2007/0028924 A1 | 2/2007 | Madsen et al. |
| 2007/0038226 A1 | 2/2007 | Galdonik et al. |
| 2007/0089748 A1 | 4/2007 | Madsen et al. |
| 2007/0163599 A1 | 7/2007 | Mijers |
| 2007/0282250 A1 | 12/2007 | Anderson et al. |
| 2008/0011304 A1 | 1/2008 | Stewart |
| 2008/0035154 A1 | 2/2008 | Johnson |
| 2008/0047562 A1 | 2/2008 | Colburn et al. |
| 2008/0066746 A1 | 3/2008 | Nelson et al. |
| 2008/0114338 A1 | 5/2008 | Kumar |
| 2008/0121236 A1 | 5/2008 | Field |
| 2008/0167606 A1 | 7/2008 | Dann et al. |
| 2008/0210235 A1 | 9/2008 | Field et al. |
| 2009/0178681 A1 | 7/2009 | Bracken |
| 2009/0260632 A1 | 10/2009 | Abnousi et al. |
| 2009/0281483 A1 | 11/2009 | Baker et al. |
| 2009/0287151 A1 | 11/2009 | Resca |
| 2010/0010431 A1 | 1/2010 | Tulley |
| 2010/0036410 A1 | 2/2010 | Krolik et al. |
| 2010/0081896 A1 | 4/2010 | Swisher |
| 2010/0106102 A1 | 4/2010 | Ziebol et al. |
| 2010/0113916 A1 | 5/2010 | Kumar |
| 2010/0137899 A1 | 6/2010 | Razack |
| 2010/0147309 A1 | 6/2010 | Cuevas et al. |
| 2010/0147310 A1 | 6/2010 | Brewer et al. |
| 2010/0147312 A1 | 6/2010 | Brewer et al. |
| 2010/0170517 A1 | 7/2010 | Hackner |
| 2010/0186748 A1 | 7/2010 | Morejon |
| 2010/0199448 A1 | 8/2010 | Vazales et al. |
| 2010/0199999 A1 | 8/2010 | Vazales et al. |
| 2010/0307507 A1 | 12/2010 | Li et al. |
| 2010/0307508 A1 | 12/2010 | Li et al. |
| 2011/0023884 A1 | 2/2011 | Cuevas et al. |
| 2011/0023885 A1 | 2/2011 | Vazales et al. |
| 2011/0023886 A1 | 2/2011 | Vazales et al. |
| 2011/0023887 A1 | 2/2011 | Vazales et al. |
| 2011/0023888 A1 | 2/2011 | Vazales et al. |
| 2011/0180072 A1 | 7/2011 | Morejon |
| 2011/0186052 A1 | 8/2011 | Morejon |
| 2011/0197894 A1 | 8/2011 | Morejon |
| 2011/0247412 A1 | 10/2011 | Scott |
| 2011/0253145 A1 | 10/2011 | Calderoni et al. |
| 2012/0024293 A1 | 2/2012 | Maguire et al. |
| 2012/0090619 A1 | 4/2012 | Levine |
| 2012/0180791 A1 | 7/2012 | Ciccone |
| 2012/0204884 A1 | 8/2012 | Howard |
| 2012/0247479 A1 | 10/2012 | Varga et al. |
| 2012/0289893 A1 | 11/2012 | Ch Ung |
| 2012/0296283 A1 | 11/2012 | Swisher |
| 2013/0014756 A1 | 1/2013 | Young et al. |
| 2013/0023729 A1 | 1/2013 | Vazales et al. |
| 2013/0030249 A1 | 1/2013 | Vazales et al. |
| 2013/0035628 A1 | 2/2013 | Garrison et al. |
| 2013/0046332 A1 | 2/2013 | Jones et al. |
| 2013/0112207 A1 | 5/2013 | Roth |
| 2013/0146063 A1 | 6/2013 | Sederstrom et al. |
| 2013/0218071 A1 | 8/2013 | Resca |
| 2013/0228196 A1 | 9/2013 | Vazales et al. |
| 2014/0012074 A1 | 1/2014 | Vazales et al. |
| 2014/0020682 A1 | 1/2014 | Li et al. |
| 2014/0033455 A1 | 2/2014 | Vazales et al. |
| 2014/0090194 A1 | 4/2014 | Stadelman et al. |
| 2014/0090195 A1 | 4/2014 | Stadelman et al. |
| 2014/0090642 A1 | 4/2014 | Bagwell et al. |
| 2014/0142496 A1 | 5/2014 | Zachar et al. |
| 2014/0150782 A1 | 6/2014 | Vazales et al. |
| 2014/0196721 A1 | 7/2014 | Gilhuly |
| 2014/0246015 A1 | 9/2014 | Einav et al. |
| 2014/0283875 A1 | 9/2014 | Vazales et al. |
| 2014/0290649 A1 | 10/2014 | Maguire et al. |
| 2015/0133864 A1 | 5/2015 | Zachar et al. |
| 2015/0190597 A1 | 7/2015 | Zachar et al. |
| 2015/0209536 A1 | 7/2015 | Roth |
| 2015/0335842 A1 | 11/2015 | Cuevas et al. |
| 2015/0343182 A1* | 12/2015 | Vazales .................. A61B 1/122 |
| | | 604/267 |
| 2016/0082212 A1 | 3/2016 | Li et al. |
| 2016/0121066 A1 | 5/2016 | Zachar et al. |
| 2016/0193011 A1 | 7/2016 | Vazales et al. |
| 2016/0193439 A1 | 7/2016 | Zachar et al. |
| 2016/0199608 A1 | 7/2016 | Morejon |
| 2016/0250431 A1 | 9/2016 | Sederstrom et al. |
| 2016/0287834 A1 | 10/2016 | Bennett |
| 2017/0106160 A1 | 4/2017 | Zachar |
| 2017/0189589 A1 | 7/2017 | Zachar et al. |
| 2017/0326317 A1 | 11/2017 | Zachar |

FOREIGN PATENT DOCUMENTS

| | | |
|---|---|---|
| EP | 2928517 A1 | 10/2015 |
| GB | 2482618 A | 2/2012 |
| JP | 2009504240 A | 2/2009 |
| WO | WO8907466 A1 | 8/1989 |
| WO | WO9403226 A1 | 2/1994 |
| WO | 99/38548 A2 | 8/1999 |
| WO | WO9938548 A2 | 8/1999 |
| WO | WO03101516 A1 | 12/2003 |
| WO | WO2006099434 A1 | 9/2006 |
| WO | WO2007024288 A1 | 3/2007 |
| WO | 2007/141787 A1 | 12/2007 |
| WO | WO2007146613 A2 | 12/2007 |
| WO | WO2010091309 A1 | 8/2010 |
| WO | WO2011020985 A1 | 2/2011 |
| WO | WO2011094517 A1 | 8/2011 |
| WO | WO2011126812 A1 | 10/2011 |
| WO | 2012087837 A1 | 6/2012 |
| WO | WO2012131626 A2 | 10/2012 |
| WO | WO2013030821 A1 | 3/2013 |
| WO | WO2014089028 A1 | 6/2014 |
| WO | WO2015187583 A1 | 12/2015 |
| WO | 2017118970 A1 | 7/2017 |
| WO | 2017199248 A1 | 11/2017 |

OTHER PUBLICATIONS

International Search Report and Written Opinion for PCT/IL2017/50284 dated Jun. 9, 2017.
International Search Report and Written Opinion for PCT/IL2016/51367 dated May 26, 2017.
U.S. Appl. No. 61/468,990, filed Mar. 29, 2011.
U.S. Appl. No. 61/473,790, filed Apr. 10, 2011.
U.S. Appl. No. 61/483,699, filed May 8, 2011.
U.S. Appl. No. 61/496,019, filed Jun. 12, 2011.
U.S. Appl. No. 61/527,658, filed Aug. 26, 2011.
U.S. Appl. No. 61/539,998, filed Sep. 28, 2011.
U.S. Appl. No. 61/560,385, filed Nov. 16, 2011.
U.S. Appl. No. 61/603,340, filed Feb. 26, 2012.
U.S. Appl. No. 61/603,344, filed Feb. 26, 2012.
U.S. Appl. No. 61/609,763, filed Mar. 12, 2012.
U.S. Appl. No. 61/613,408, filed Mar. 20, 2012.
U.S. Appl. No. 61/635,360, filed Apr. 19, 2012.
U.S. Appl. No. 61/655,801, filed Jun. 5, 2012.
U.S. Appl. No. 61/660,832, filed Jun. 18, 2012.
U.S. Appl. No. 61/673,744, filed Jul. 20, 2012.
Machine Translation JP 2009504240 (by EPO and Google)—published Feb. 5, 2009; Kimberly-Clark Worldwide Inc.
Search Report dated Nov. 2, 2011 which issued during the prosecution of GB Patent Application No. 2482618.
Duguet A et al., "Control of tracheal cuff pressure: a pilot study using a pneumatic device," Intensive Care Med. Jan. 2007;33(1):128-32.

(56) References Cited

OTHER PUBLICATIONS

Maggiore SM et al., "Closed versus open suctioning techniques," Minerva Anestesiol. May 2002;68(5):360-4.
International Search Report for PCT/IL2012/000320, dated Nov. 15, 2012.
Written Opinion for PCT/IL2012/000320, dated Nov. 15, 2012.
International Search Report for PCT/IB2012/051532, dated Oct. 16, 2012.
Office Action for U.S. Appl. No. 14/596,905, dated Jul. 21, 2015.
Office Action for U.S. Appl. No. 13/806,958, dated Jun. 11, 2014.
Office Action for U.S. Appl. No. 13/806,958, dated Nov. 10, 2014.
Office Action together with the English translation dated Jan. 26, 2016, which issued during the prosecution Japanese Patent Application No. 2014-501798.
Office Action together with the English translation dated May 24, 2016, which issued during the prosecution of Japanese Patent Application No. 2014-526598.
European Search Report dated Jan. 14, 2016, which issued during the prosecution of Applicant's European App No. 12828334.
Examination Report dated Nov. 3, 2011 which issued during the prosecution of GB Patent Application No. 1116735.0.
Notice of Allowance Action dated Dec. 2, 2014, which issued during the prosecution of U.S. Appl. No. 13/806,958.
Novelty Search Report dated Sep. 16, 2011 which issued during the prosecution of Swedish Patent Application No. 179871.
Search Report dated Jun. 6, 2016, which issued during the prosecution of GB Patent Application No. 1600233.9.

\* cited by examiner

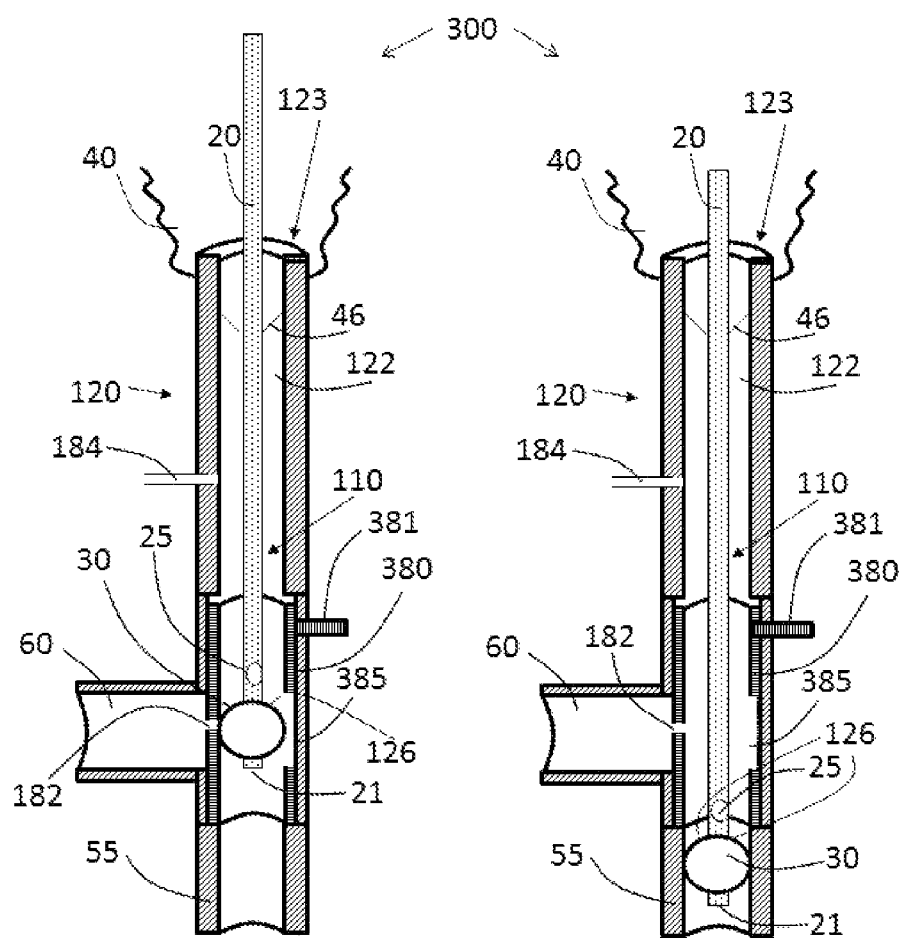

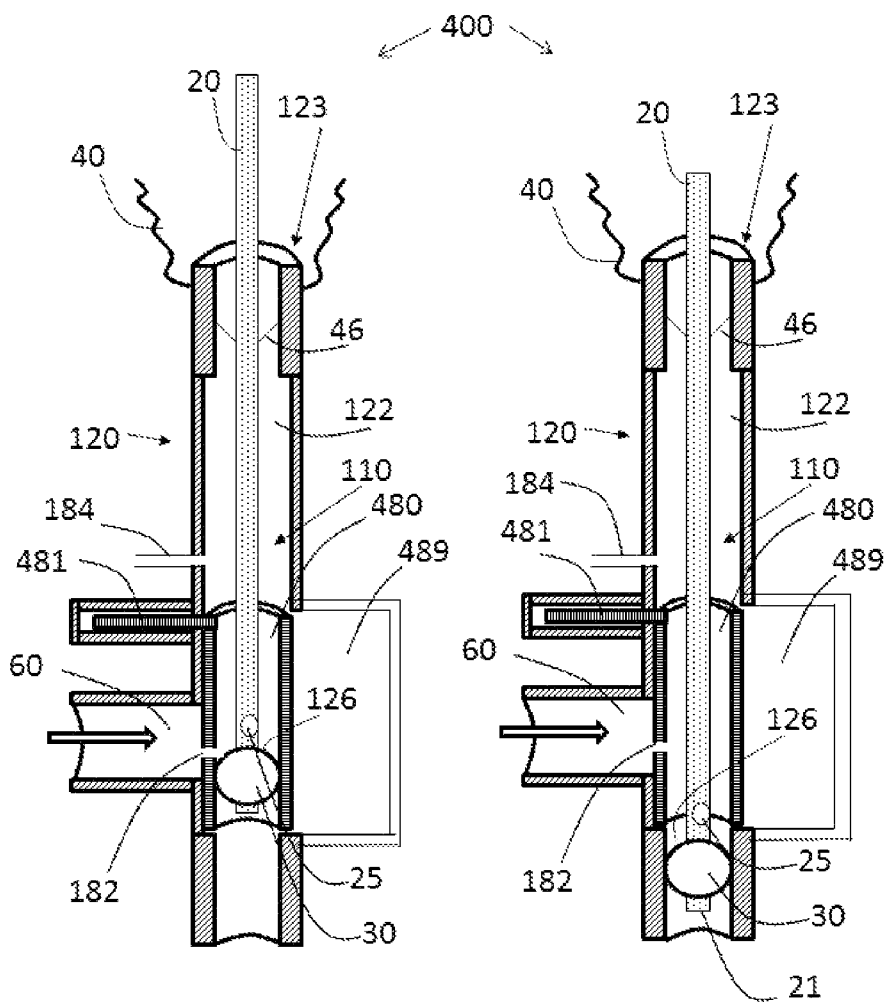

CATHETER FOR CLEANING OF TRACHEAL VENTILATION TUBES

CROSS REFERENCE TO RELATED APPLICATIONS

The patent application is a non-provisional of U.S. provisional application Ser. No. 62/043,428 filed on Aug. 27, 2014 which is hereby incorporated in its entirety by reference.

FIELD OF THE APPLICATION

The present invention relates generally to medical suction catheter devices, and specifically to catheter devices for aspiration of tracheobronchial secretions and/or cleaning of tracheal ventilation tubes.

BACKGROUND OF THE APPLICATION

Suction catheters are commonly used to aspirate tracheobronchial fluids in patients ventilated with endotracheal tube (ETT) and tracheostomy tube devices. A problematic aspect of the use of suction catheters is the presence of bacterial biofilm within the ETT lumen which may contribute to lung infection. Moreover, buildup of substantial biofilm thickness reduces the effective free lumen of the ETT for air passage. Therefore, there is a need for maintaining cleaner ETT lumens and preventing buildup of significant biofilm thickness.

UK Publication GB 2482618 A to Einav et al., which is assigned to the assignee of the present application and is incorporated herein by reference, describes a multi-lumen catheter for multiple fluids conduction, including balloon inflation with air via an inflation lumen, suction via a suction lumen, and cleaning fluids delivery via a cleaning fluid-delivery lumen.

PCT Publication WO/2012/131626 to Einav et al., which is assigned to the assignee of the present application and is incorporated herein by reference, describes a cleaning device, system and method for use with an ETT or tracheostomy ventilation tube, a ventilator machine, a source(s) of fluid (for example, pressurized or unpressurized) and a source(s) of suctioning. In some embodiments, the cleaning device is useful for cleaning an inner surface of the ventilation tube and/or for preventing or hindering the accumulation of biofilm thereon. In some embodiments, it is possible to clean biofilm or any other material on the inner surface by delivering fluid into an interior of the ventilation tube, wiping the tube interior with a width-expanded wiping element (e.g. an inflated balloon) by longitudinal motion of the wiping element, and suctioning material out of the ventilation tube ventilation tube.

U.S. Pat. No. 7,051,737 to Kolobow et al. describes an endotracheal tube cleaning apparatus which can be periodically inserted into the inside of an endotracheal tube to shave away mucus deposits. In a preferred embodiment, this cleaning apparatus comprises a flexible central tube with an inflatable balloon at its distal end. Affixed to the inflatable balloon are one or more shaving rings, each having a squared leading edge, to shave away mucus accumulations. In operation, the uninflated cleaning apparatus is inserted into the endotracheal tube. The balloon is then inflated by a suitable inflation device, such as a syringe, until the balloon's shaving rings are pressed against the inside surface of the endotracheal tube. The cleaning apparatus is then pulled out of the endotracheal tube to shave off mucus deposits.

PCT Publication WO 2013/030821 to Zachar et al., which is assigned to the assignee of the present application and is incorporated herein by reference, describes a cleaning catheter that includes fluid-delivery and suction lumens. A flow regulator defines suction and fluid ports. A mechanical user control element is configured to mechanically and non-electrically set activation states of the flow regulator, and transition between first and third configurations via a second configuration. When the control element is in the first configuration, the flow regulator blocks fluid communication (a) between the suction port and the suction lumen and (b) between the fluid port and the fluid-delivery lumen. When the control element is in the second configuration, the flow regulator effects fluid communication between the suction port and the suction lumen, and blocks fluid communication between the fluid port and the fluid-delivery lumen. When the control element is in the third configuration, the flow regulator effects fluid communication (a) between the suction port and the suction lumen and (b) between the fluid port and the fluid-delivery lumen.

SUMMARY OF THE APPLICATION

In embodiments of the present invention, a suction cleaning system component is provided for use in cleaning an interior of a tracheal ventilation tube when the suction cleaning system component is connected to the tracheal ventilation tube and a ventilator. Typically, the suction cleaning system component is used in a closed endotracheal suction system environment. The suction cleaning system component comprises a cleaning catheter and a manifold. The cleaning catheter comprises an elongate tube and an expandable element, which is mounted to the elongate tube near a distal end of the elongate tube, and is expandable into contact with an inner surface of the tracheal ventilation tube.

The manifold is shaped so as to define:
  a tubular chamber, which is shaped so as to allow passage therethrough of the cleaning catheter, and which has an inlet for the cleaning catheter at a proximal end of the tubular chamber;
  a ventilator port in a lateral wall of the tubular chamber; the ventilator port is configured to be coupled in fluid communication with the ventilator; and
  a tracheal ventilation tube port, which is configured to be coupled in fluid communication with a proximal end of the tracheal ventilation tube.

The manifold comprises an obstruction element, which is moveable with respect to (i) the ventilator port and (ii) the expandable element. The obstruction element is configured to assume a plurality of states, including an obstruction state. In the obstruction state, the obstruction element, at least during proximal withdrawal of the expandable element past the ventilator port while the expandable element is expanded, inhibits air flow between the ventilator port and at least a portion of a proximally-facing external surface of the expandable element.

During use, the cleaning catheter is first advanced distally through the tubular chamber, and then through the tracheal ventilation tube to or slightly beyond the distal end of the tracheal ventilation tube. During this distal advancement, the expandable element is in a non-expanded state (i.e., not in full contact with circumference of the inner surface of the tracheal ventilation tube). For cleaning operation, the expandable element is then expanded, which induces contact between a portion of the outer surface of the expandable element and the inner surface of the tracheal ventilation tube. While thus expanded, the expandable element is then withdrawn proximally through the tracheal ventilation tube, such that the portion of the outer surface of the expandable element wipes the inner wall of the tracheal ventilation tube. Typically, during this proximal withdrawal, suction is applied by a suction source via one or more distal suction orifices of the cleaning catheter, in order to remove the debris (which typically includes bacterial biofilm) wiped off of the inner wall of the tracheal ventilation tube by the expandable element. The one or more distal suction orifices are disposed proximally to the expandable element, and are in fluid connection with the suction source via the elongate tube.

Before the proximal withdrawal of the expandable element past the ventilator port, the obstruction element is positioned in the obstruction state. During proximal withdrawal of the expandable element past the ventilator port while the expandable element is expanded, the obstruction element inhibits air flow between the ventilator port and the at least a portion of the proximally-facing external surface of the expandable element. In the absence of the obstruction element, the air pressure from the ventilator port might dislodge debris from the at least a portion of the proximally-facing external surface of the expandable element during the proximal withdrawal of the expandable element past the ventilator port, and propel the debris distally around expandable element, through the tracheal ventilation tube, and into the patient's lungs. After the expandable element has been withdrawn proximally beyond the ventilator port, the obstruction element is moved out of the obstruction state, such as into the open state described hereinbelow.

For some applications, the obstruction element is transitioned between at least a portion of the plurality of states manually by an operator of the suction cleaning system component. For example, the manifold may comprise a user-control element, such as a sliding or rotating user handle coupled to the obstruction element through the wall of the tubular chamber. For other applications, the obstruction element automatically transitions between at least a portion of the plurality of states. For example, distal advancement of the elongate tube may automatically transition the obstruction element to the obstruction state, and/or proximal withdrawal of the elongate tube may automatically transition the obstruction element out of the obstruction state.

For some applications, the manifold is configured such that the plurality of states further includes an air-flow state, in which the obstruction element, at least when the expandable element is disposed distally to the ventilator port while the expandable element is expanded, allows air flow between the ventilator port and the at least a portion of the proximally-facing external surface of the expandable element at a greater level than when the obstruction element is in the obstruction state. For applications in which it occurs, this state occurs while the expandable element is disposed distally to the ventilator port while expanded, and the obstruction element is positioned proximal to the ventilator port. For some applications, the obstruction element, when in the air-flow state, is configured to allow the air flow between the ventilator port and the at least a portion of the proximally-facing external surface of the expandable element at at least twice, e.g., at least 5 times, the level occurring when the obstruction element is in the obstruction state.

For some applications, the manifold is configured such that the obstruction element, when in the obstruction state, inhibits air flow between the ventilator port and the tubular chamber. For some applications, the manifold is configured such that the plurality of states further includes an open state. In this open state, the obstruction element allows air flow between the ventilator port and the tracheal ventilation tube via the tubular chamber, at least when the expandable element is disposed proximally to the ventilator port.

In some applications of the present invention, the obstruction element comprises a flap, which is disposed within the tubular chamber and is attached to the lateral wall of the tubular chamber, for example at or proximal to a proximal end of the ventilator port. The manifold is configured such that when the flap is in the obstruction state, the flap covers the ventilator port (not necessarily with a fluid-tight seal) and inhibits air flow between the ventilator port and the at least a portion of the proximally-facing external surface of the expandable element.

For some applications, the flap is elastically biased to an open configuration in which the flap does not cover the ventilator port. For some applications, the flap is configured to assume a partially-open state, in which state the flap allows a lower level of the air flow between the ventilator port and the at least a portion of the proximally-facing external surface of the expandable element than when the flap in the open configuration. For some applications, the flap is configured to automatically assume the partially-open state when the expandable element is disposed at a longitudinal position distal to the ventilator port. For some applications, the flap is configured to automatically assume the partially-open state or the open configuration when the expandable element is disposed at a longitudinal position distal to the ventilator port. For some applications, the elongate tube of the cleaning catheter is configured to hold the flap in the partially-open state, and prevents the flap from assuming the open configuration.

For some applications, the manifold is configured such that the proximal withdrawal of the expandable element fully over and proximally beyond the flap, while the expandable element is expanded, automatically transitions the flap out of the obstruction state. For some applications, the manifold is configured such that the proximal withdrawal of the expandable element, while the expandable element is expanded, automatically transitions the flap to the obstruction state, by the expandable element pushing the flap against the ventilator port.

For some applications, the flap is elastically biased to an open configuration in which the flap does not cover the ventilator port. For some of these applications, the manifold is configured such that the proximal withdrawal of the expandable element fully over and proximally beyond the flap, while the expandable element is expanded, allows the flap to assume the open configuration. Alternatively or additionally, for some of these applications, the proximal withdrawal of the expandable element to a first longitudinal position, while the expandable element is expanded, automatically transitions the flap to the obstruction state, and the manifold is configured such that the proximal withdrawal of the expandable element to a second longitudinal position, while the expandable element is expanded, allows the flap to assume the open configuration, the second longitudinal position being proximal to the first longitudinal position.

For some applications, the flap is shaped such that a surface of the flap facing radially inwardly, when the flap is in the obstruction state, is convex toward a central longitudinal axis of the tubular chamber. Alternatively or additionally, for some applications, the flap is shaped such that a distal portion of the flap, when the flap is in the obstruction state, is tapered toward a distal end of the flap.

In some applications of the present invention, the obstruction element comprises an open-ended tube having a longitudinal axis parallel to a longitudinal axis of the tubular chamber. For some applications, the longitudinal axis of the open-ended tube is coaxial with the longitudinal axis of the tubular chamber. For some applications, the open-ended tube is disposed within the tubular chamber; for some of these applications, the open-ended tube is longitudinally-slidably disposed within the tubular chamber.

For some applications, the tracheal ventilation tube port has a first inner perimeter and a longitudinal axis parallel to the longitudinal axis of the open-ended tube, and the open-ended tube has a second inner perimeter which is more than 90% of the first inner perimeter. As a result, the expandable element slides into the open-ended tube during the proximal withdrawal of the expandable element while the expandable element is expanded.

For some applications, the manifold is configured such that the proximal withdrawal of the expandable element, while the expandable element is expanded, automatically transitions the obstruction element out of the obstruction state.

For some applications, the tracheal ventilation tube port has a first inner perimeter (e.g., diameter) and a longitudinal axis parallel to the longitudinal axis of the open-ended tube, and the open-ended tube has a second inner perimeter (e.g., diameter) which is less than 90% of the first inner perimeter. As a result, the proximal withdrawal of the expandable element, while the expandable element is expanded (typically, to the larger first inner perimeter (e.g., diameter) of the tracheal ventilation tube port), pushes the open-ended tube proximally, thereby automatically transitioning the obstruction element out of the obstruction state.

For some applications, the open-ended tube is rotatably disposed within the tubular chamber, and a wall of the open-ended tube is shaped so as to define a the lateral fenestration, which, when the obstruction element is in the obstruction state, is not rotationally aligned with the ventilator port, so as to inhibit the air flow between the ventilator port and the at least a portion of the proximally-facing external surface of the expandable element. For some applications, the manifold is configured such that the plurality of states further includes an open state, in which the obstruction element is rotationally aligned with the ventilator port, so as to allow air flow between the ventilator port and the tracheal ventilation tube via the fenestration and the tubular chamber, at least when the expandable element is disposed proximally to the ventilator port.

For some applications, the manifold is shaped so as to define a lateral extension, at least a portion of which longitudinally overlaps the ventilator port. The manifold is configured such that when the obstruction element is in the obstruction state, the open-ended tube is coaxial with the tracheal ventilation tube port. For some applications, the manifold is configured such that the plurality of states further includes an open state, in which the open-ended tube is non-coaxial with the tracheal ventilation tube port, and is disposed at least partially within the lateral extension, so as to allow air flow between the ventilator port and the tracheal ventilation tube, at least when the expandable element is disposed proximally to the ventilator port.

In some applications of the present invention, the obstruction element comprises an arcuate portion (i.e., less than a complete circle) of a cylindrical tube having a longitudinal axis parallel to a longitudinal axis of the tubular chamber. For some applications, the arcuate portion is longitudinally-slidably disposed within the tubular chamber.

There is therefore provided, in accordance with an application of the present invention, apparatus for use with a tracheal ventilation tube and a ventilator, the apparatus including:

a cleaning catheter, which includes an elongate tube and an expandable element, which is mounted to the elongate tube, and is expandable into contact with an inner surface of the tracheal ventilation tube; and a manifold, which:

is shaped so as to define (a) a tubular chamber, which is shaped so as to allow passage therethrough of the cleaning catheter, and which has an inlet for the cleaning catheter at a proximal end of the tubular chamber, (b) a ventilator port in a lateral wall of the tubular chamber, which ventilator port is configured to be coupled in fluid communication with the ventilator, and (c) a tracheal ventilation tube port, which is configured to be coupled in fluid communication with a proximal end of the tracheal ventilation tube, and includes an obstruction element, which is (a) moveable with respect to (i) the ventilator port and (ii) the expandable element, and (b) configured to assume a plurality of states, including an obstruction state, in which state the obstruction element, at least during proximal withdrawal of the expandable element past the ventilator port while the expandable element is expanded, inhibits air flow between the ventilator port and at least a portion of a proximally-facing external surface of the expandable element.

For some applications, the manifold is configured such that the obstruction element, when in the obstruction state, inhibits air flow between the ventilator port and the tubular chamber.

For some applications, the expandable element includes an inflatable element, such as an inflatable balloon.

For some applications, the expandable element is mounted to the elongate tube at a site along a distal-most portion of the elongate tube, which distal-most portion has a length equal to 30% of a total length of the elongate tube.

For some applications, the expandable element is mounted to the elongate tube at a site within 20 mm of a distal end of the elongate tube.

For some applications, the apparatus is for use with a suction source, and a distal portion of the cleaning catheter includes one or more distal suction orifices, which are disposed proximally to the expandable element, and which are in fluid connection with the suction source.

For some applications, the obstruction element is shaped so as to define a lateral opening having a cross-sectional area of between 1 mm2 and 25 mm2.

For any of the applications described above, the manifold may be configured such that the plurality of states further includes an air-flow state, in which state the obstruction element, at least when the expandable element is disposed distally to the ventilator port while the expandable element is expanded, allows air flow between the ventilator port and the at least a portion of the proximal surface of the expandable element at a greater level than when the obstruction element is in the obstruction state. For some applications, the obstruction element, when in the air-flow state, is configured to allow the air flow between the ventilator port and the at least a portion of the proximal surface of the expandable element at at least twice the level occurring when the obstruction element is in the obstruction state. For some applications, the obstruction element, when in the air-flow, is configured to allow the air flow between the ventilator port and the at least a portion of the proximal surface of the expandable element at at least 5 times the level occurring when the obstruction element is in the obstruction state.

For any of the applications described above, the manifold may be configured such that the plurality of states further includes an open state, in which state the obstruction element allows air flow between the ventilator port and the tracheal ventilation tube via the tubular chamber, at least when the expandable element is disposed proximally to the ventilator port. For some applications, the manifold is configured such that the obstruction element, when in the obstruction state in at least some longitudinal positions with respect to the ventilator port, allows a lower level of the air flow between the ventilator port and the tracheal ventilation tube than when the obstruction element is in the open state.

For any of the applications described above, the manifold may be configured such that the proximal withdrawal of the expandable element, while the expandable element is expanded, automatically transitions the obstruction element out of the obstruction state. For some applications, the manifold is configured such that: the plurality of states further includes an open state, in which state the obstruction element allows air flow between the ventilator port and the tracheal ventilation tube via the tubular chamber, at least when the expandable element is disposed proximally to the ventilator port; and the proximal withdrawal of the expandable element, while the expandable element is expanded, automatically transitions the obstruction element out of the obstruction state into the open state.

For any of the applications described above, the manifold may be configured such that at least one site of the obstruction element is longitudinally fixed with respect to the tubular chamber.

For any of the applications described above, the obstruction element may include a flap, which is disposed within the tubular chamber and is attached to the lateral wall of the tubular chamber; and the manifold may be configured such that when the flap is in the obstruction state, the flap covers the ventilator port and inhibits air flow between the ventilator port and the at least a portion of the proximally-facing external surface of the expandable element. For some applications, the flap is attached to the lateral wall at or proximal to a proximal end of the ventilator port. For some applications, the flap is elastically biased to an open configuration in which the flap does not cover the ventilator port. For some applications, the flap is configured to assume a partially-open state, in which state the flap allows a lower level of the air flow between the ventilator port and the at least a portion of the proximally-facing external surface of the expandable element than when the flap in the open configuration.

For some applications, the flap is configured to automatically assume the partially-open state when the expandable element is disposed at a longitudinal position distal to the ventilator port. For some applications, the flap is configured to automatically assume the partially-open state or the open configuration when the expandable element is disposed at a longitudinal position distal to the ventilator port.

For some applications, the elongate tube of the cleaning catheter is configured to hold the flap in the partially-open state, and prevents the flap from assuming the open configuration.

For some applications, the manifold is configured such that the proximal withdrawal of the expandable element, while the expandable element is expanded, automatically transitions the flap to the obstruction state, by the expandable element pushing the flap against the ventilator port.

For some applications, the manifold is configured such that the proximal withdrawal of the expandable element fully over and proximally beyond the flap, while the expandable element is expanded, automatically transitions the flap out of the obstruction state.

For some applications, the flap is elastically biased to an open configuration in which the flap does not cover the ventilator port, and the manifold is configured such that the proximal withdrawal of the expandable element fully over and proximally beyond the flap, while the expandable element is expanded, allows the flap to assume the open configuration.

For some applications:

the manifold is configured such that the proximal withdrawal of the expandable element to a first longitudinal position, while the expandable element is expanded, automatically transitions the flap to the obstruction state, the flap is elastically biased to an open configuration in which the flap does not cover the ventilator port, and the manifold is configured such that the proximal withdrawal of the expandable element to a second longitudinal position, while the expandable element is expanded, allows the flap to assume the open configuration, the second longitudinal position being proximal to the first longitudinal position.

For some applications, the flap is shaped such that a surface of the flap facing radially inwardly, when the flap is in the obstruction state, is convex toward a central longitudinal axis of the tubular chamber.

For some applications, the flap is shaped such that a distal portion of the flap, when the flap is in the obstruction state, is tapered toward a distal end of the flap.

For any of the applications described above, the obstruction element may include an open-ended tube having a longitudinal axis parallel to a longitudinal axis of the tubular chamber. For some applications, the open-ended tube is disposed within the tubular chamber. For some applications, the open-ended tube is longitudinally-slidably disposed within the tubular chamber. For some applications, the manifold is configured such that the obstruction element, when in the obstruction state, inhibits air flow between the ventilator port and the tubular chamber. For some applications, the manifold is configured such that the proximal withdrawal of the expandable element, while the expandable element is expanded, automatically transitions the obstruction element out of the obstruction state.

For some applications, the manifold is configured such that:

the plurality of states further includes an open state, in which state the obstruction element allows air flow between the ventilator port and the tracheal ventilation tube via the tubular chamber, at least when the expandable element is disposed proximally to the ventilator port, and the proximal withdrawal of the expandable element, while the expandable element is expanded, automatically transitions the obstruction element out of the obstruction state into the open state.

For some applications, the manifold includes a user-control handle, which is fixed to the open-ended tube and extends outside of the tubular chamber, and is configured to longitudinally slide the open-ended tube within the tubular chamber.

For some applications, the tracheal ventilation tube port has a first inner perimeter and a longitudinal axis parallel to the longitudinal axis of the open-ended tube, and the open-ended tube has a second inner perimeter which is less than 90% of the first inner perimeter, such that the proximal withdrawal of the expandable element, while the expandable element is expanded, pushes the open-ended tube proximally, thereby automatically transitioning the obstruction element out of the obstruction state.

For some applications, the tracheal ventilation tube port has a first inner perimeter and a longitudinal axis parallel to the longitudinal axis of the open-ended tube, and the open-ended tube has a second inner perimeter which is more than 90% of the first inner perimeter, such that the expandable element slides into the open-ended tube during the proximal withdrawal of the expandable element while the expandable element is expanded.

For some applications, the manifold is configured such that:

the plurality of states further includes an open state, in which state the obstruction element allows air flow between the ventilator port and the tracheal ventilation tube via the tubular chamber, at least when the expandable element is disposed proximally to the ventilator port, and the obstruction element, when in the obstruction state in at least some longitudinal positions with respect to the ventilator port, is also in a partially-open state, in which state the obstruction element allows a lower level of the air flow between the ventilator port and the tracheal ventilation tube than when the obstruction element is in the open state.

For some applications, the open-ended tube is rotatably disposed within the tubular chamber, and a wall of the open-ended tube is shaped so as to define a lateral fenestration, which, when the obstruction element is in the obstruction state, is not rotationally aligned with the ventilator port, so as to inhibit the air flow between the ventilator port and the at least a portion of the proximally-facing external surface of the expandable element.

For some applications, the manifold is configured such that the plurality of states further includes an open state, in which state the obstruction element is rotationally aligned with the ventilator port, so as to allow air flow between the ventilator port and the tracheal ventilation tube via the fenestration and the tubular chamber, at least when the expandable element is disposed proximally to the ventilator port.

For some applications, the manifold includes a user-control handle, which is fixed to the open-ended tube and extends outside of the tubular chamber, and is configured to rotate the open-ended tube within the tubular chamber.

For some applications, the manifold is shaped so as to define a lateral extension, at least a portion of which longitudinally overlaps the ventilator port; and the manifold is configured such that when the obstruction element is in the obstruction state, the open-ended tube is coaxial with the tracheal ventilation tube port.

For some applications, the manifold is configured such that the plurality of states further includes an open state, in which the open-ended tube is non-coaxial with the tracheal ventilation tube port, and is disposed at least partially within the lateral extension, so as to allow air flow between the ventilator port and the tracheal ventilation tube, at least when the expandable element is disposed proximally to the ventilator port.

For some applications, the manifold includes a user-control handle, which is fixed to the open-ended tube and extends outside of the tubular chamber, and is configured to laterally move the open-ended tube into and out of the lateral extension.

For any of the applications described above, the obstruction element may include an arcuate portion of a cylindrical tube having a longitudinal axis parallel to a longitudinal axis of the tubular chamber. For some applications, the arcuate portion is longitudinally-slidably disposed within the tubular chamber. For some applications, the manifold includes a user-control handle, which is fixed to the arcuate portion and extends outside of the tubular chamber, and is configured to longitudinally slide the arcuate portion within the tubular chamber.

There is further provided, in accordance with an application of the present invention, apparatus for use with a tracheal ventilation tube and a ventilator, the apparatus including:

a cleaning catheter, which includes an elongate tube and an expandable element, which is mounted to the elongate tube, and is expandable into contact with an inner surface of the tracheal ventilation tube; and a manifold, which:

is shaped so as to define (a) a tubular chamber, which is shaped so to allow passage therethrough of the cleaning catheter, and which has an inlet for the cleaning catheter at a proximal end of the tubular chamber, (b) a ventilator port in a lateral wall of the tubular chamber, which ventilator port is configured to be coupled in fluid communication with the ventilator, and (c) a tracheal ventilation tube port, which is configured to be coupled in fluid communication with a proximal end of the tracheal ventilation tube, and includes a flap which is (a) disposed within the tubular chamber, (b) attached to the lateral wall of the tubular chamber, and (c) configured to assume a plurality of states, including an obstruction state, in which state the flap covers the ventilator port and inhibits air flow between the ventilator port and at least a portion of a proximally-facing external surface of the expandable element.

For some applications, the manifold is configured such that the flap, when in the obstruction state, inhibits air flow between the ventilator port and the tubular chamber.

For some applications, the flap is attached to the lateral wall at or proximal to a proximal end of the ventilator port.

For some applications:

the manifold is configured such that the proximal withdrawal of the expandable element to a first longitudinal position, while the expandable element is expanded, automatically transitions the flap to the obstruction state, the flap is elastically biased to an open configuration in which the flap does not cover the ventilator port, and the manifold is configured such that the proximal withdrawal of the expandable element to a second longitudinal position, while the expandable element is expanded, allows the flap to assume the open configuration, the second longitudinal position being proximal to the first longitudinal position.

For some applications, the flap is shaped such that a surface of the flap facing radially inwardly, when the flap is in the obstruction state, is convex toward a central longitudinal axis of the tubular chamber.

For some applications, the flap is shaped such that a distal portion of the flap, when the flap is in the obstruction state, is tapered toward a distal end of the flap.

For some applications, the expandable element is mounted to the elongate tube at a site along a distal-most portion of the elongate tube, which distal-most portion has a length equal to 30% of a total length of the elongate tube.

For some applications, the expandable element is mounted to the elongate tube at a site within 20 mm of a distal end of the elongate tube.

For some applications, the expandable element includes an inflatable element, such as an inflatable balloon.

For some applications, the apparatus is for use with a suction source, and a distal portion of the cleaning catheter includes one or more distal suction orifices, which are disposed proximally to the expandable element, and which are in fluid connection with the suction source.

For any of the applications described above, the manifold is configured such that the plurality of states further includes an air-flow state, in which state the flap, at least when the expandable element is disposed distally to the ventilator port while the expandable element is expanded, allows air flow between the ventilator port and the at least a portion of the proximal surface of the expandable element at a greater level than when the flap is in the obstruction state.

For some applications, the flap, when in the air-flow state, is configured to allow the air flow between the ventilator port and the at least a portion of proximal surface of the expandable element at at least twice the level occurring when the flap is in the obstruction state.

For some applications, the flap, when in the air-flow state, is configured to allow the air flow between the ventilator port and the at least a portion of the proximal surface of the expandable element at at least 5 times the level occurring when the flap is in the obstruction state.

For any of the applications described above, the flap may be elastically biased to an open configuration in which the flap does not cover the ventilator port. For some applications, the flap is configured to assume a partially-open state, in which state the flap allows a lower level of the air flow between the ventilator port and the at least a portion of the proximally-facing external surface of the expandable element than when the flap is in the open configuration. For some applications, the flap is configured to automatically assume the partially-open state when the expandable element is disposed at a longitudinal position distal to the ventilator port. For some applications, the flap is configured to automatically assume the partially-open state or the open configuration when the expandable element is disposed at a longitudinal position distal to the ventilator port. For some applications, the elongate tube of the cleaning catheter is configured to hold the flap in the partially-open state, and prevents the flap from assuming the open configuration.

For any of the applications described above, the manifold may be configured such that the proximal withdrawal of the expandable element, while the expandable element is expanded, automatically transitions the flap to the obstruction state, by the expandable element pushing the flap against the ventilator port.

For any of the applications described above, the manifold may be configured such that the proximal withdrawal of the expandable element, while the expandable element is expanded, automatically transitions the flap out of the obstruction state. For some applications, the flap is elastically biased to an open configuration in which the flap does not cover the ventilator port; and the manifold is configured such that the proximal withdrawal of the expandable element fully over and proximally beyond the flap, while the expandable element is expanded, allows the flap to assume the open configuration.

There is still further provided, in accordance with an application of the present invention, a method for use with a tracheal ventilation tube and a ventilator, the method including:

coupling, in fluid communication with a proximal end of the tracheal ventilation tube, a tracheal ventilation tube port of a manifold;

coupling, in fluid communication with the ventilator, a ventilator port in a lateral wall of a tubular chamber of the manifold, wherein the manifold includes an obstruction element, which is (a) moveable with respect to (i) the ventilator port and (ii) the expandable element, and (b) configured to assume a plurality of states;

advancing a cleaning catheter through a proximal-end inlet of the tubular chamber and into the tracheal ventilation tube inserted in a trachea of a patient, which cleaning catheter includes an elongate tube and an expandable element, which is mounted to the elongate tube;

expanding the expandable element into contact with an inner surface of the tracheal ventilation tube;

transitioning the obstruction element to an obstruction state of the plurality of the states, in which state the obstruction element, at least during proximal withdrawal of the expandable element past the ventilator port while the expandable element is expanded, inhibits air flow between the ventilator port and at least a portion of a proximally-facing external surface of the expandable element; and proximally withdrawing the expandable element past the ventilator port while the expandable element is expanded.

There is additionally provided, in accordance with an application of the present invention, a method for use with a tracheal ventilation tube and a ventilator, the method including:

coupling, in fluid communication with a proximal end of the tracheal ventilation tube, a tracheal ventilation tube port of a manifold;

coupling, in fluid communication with the ventilator, a ventilator port in a lateral wall of a tubular chamber of the manifold, wherein the manifold includes a flap which is (a) disposed within the tubular chamber, (b) attached to the lateral wall of the tubular chamber, and (c) configured to assume a plurality of states;

advancing a cleaning catheter through a proximal-end inlet of the tubular chamber and into the tracheal ventilation tube inserted in a trachea of a patient, which cleaning catheter includes an elongate tube and an expandable element, which is mounted to the elongate tube;

expanding the expandable element into contact with an inner surface of the tracheal ventilation tube;

transitioning the flap to an obstruction state of the plurality of the states, in which state the flap covers the ventilator port and inhibits air flow between the ventilator port and at least a portion of a proximally-facing external surface of the expandable element; and proximally withdrawing the expandable element past the ventilator port while the expandable element is expanded.

The present invention will be more fully understood from the following detailed description of embodiments thereof, taken together with the drawings, in which:

BRIEF DESCRIPTION OF THE DRAWINGS

FIGS. 3A-C are schematic illustrations of yet another suction cleaning system component, in accordance with an application of the present invention;

FIGS. 4A-C are schematic illustrations of still another suction cleaning system component, in accordance with an application of the present invention;

DETAILED DESCRIPTION OF APPLICATIONS

Figures 1A, 1B:
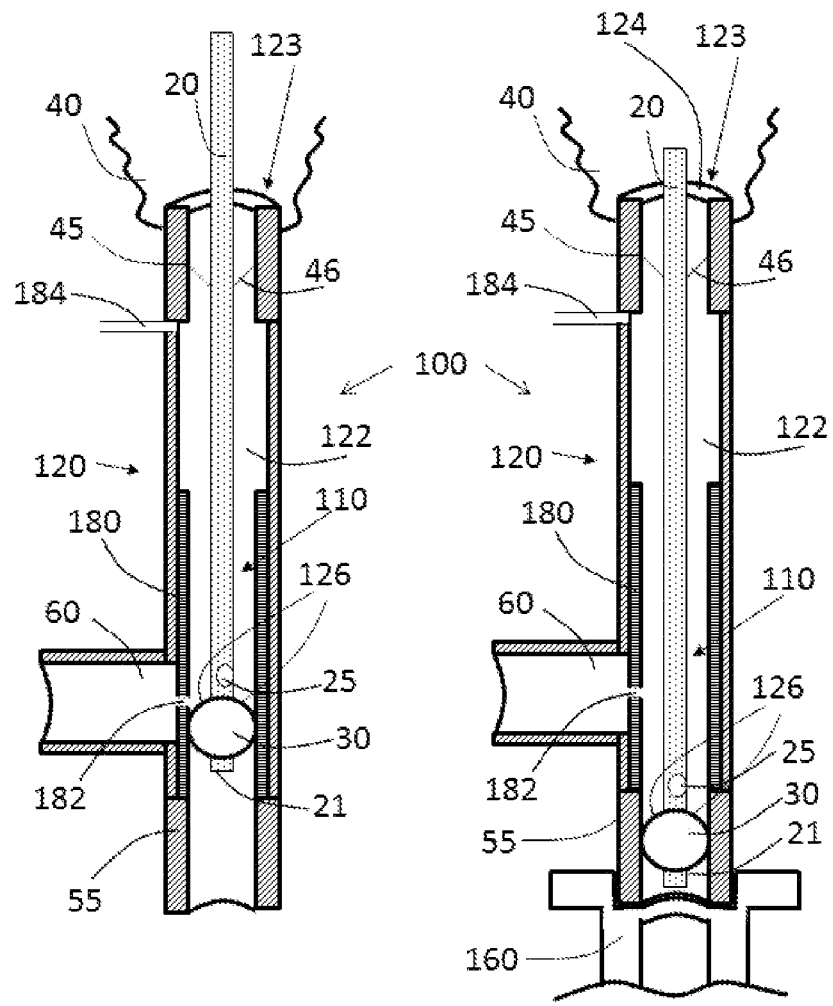
FIGS. 1A-C are schematic illustrations of a suction cleaning system component, in accordance with an application of the present invention.
Figure 1C:
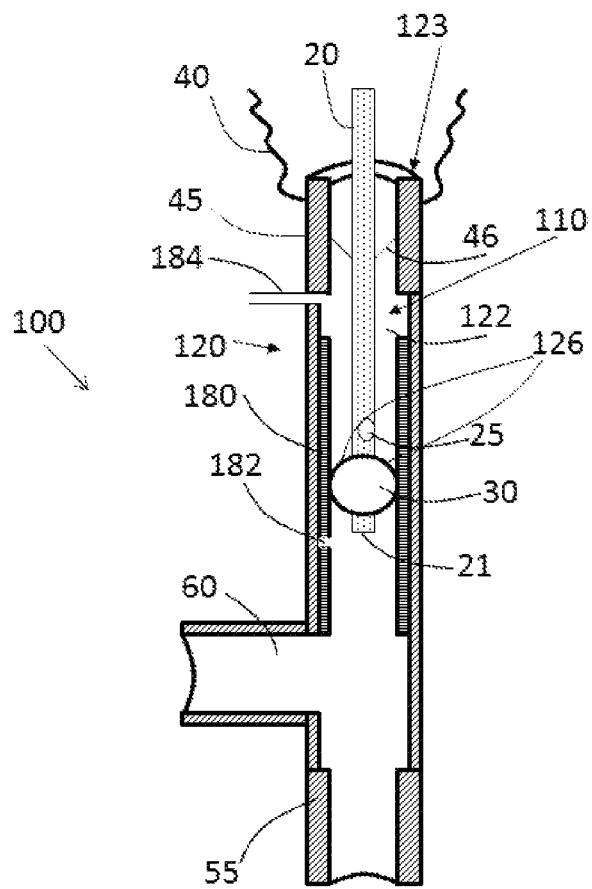
Figure 1D:
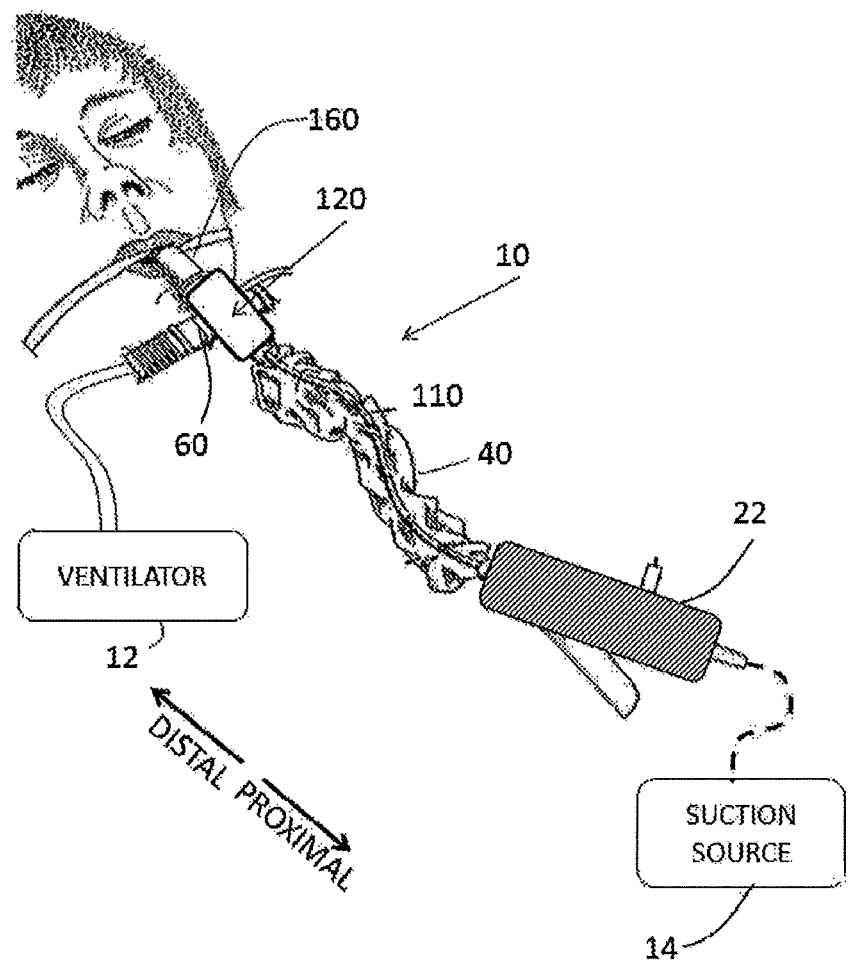
FIG. 1D is a schematic illustration of a closed suction system cleaning system, in accordance with an application of the present invention.

FIG. 1D is a schematic illustration of a closed suction system cleaning system 10, in accordance with an application of the present invention. Suction cleaning system 10 is configured for use with a tracheal ventilation tube 160, a ventilator 12, a suction source 14, and, optionally, an inflation source, which may comprise, for example, a conventional syringe. Cleaning system 10 comprises a suction cleaning system component 100; a flexible, a cleaning catheter 20; and an input module 22.

FIGS. 1A-C are schematic illustrations of suction cleaning system component 100 of closed suction system cleaning system 10, in accordance with an application of the present invention. Suction cleaning system component 100 is configured for use with tracheal ventilation tube 160, ventilator 12, suction source 14, and, optionally, the inflation source. (For clarity of illustration, tracheal ventilation tube 160 is shown only in FIGS. 1A and 1D, although it is in practice present in the configurations shown in all of the figures.)

As used in the present application, including in the claims, a "tracheal ventilation tube" comprises an endotracheal tube (ETT) or a tracheostomy tube. The suction source typically provides a pressure less than one atm. As used in the present application, including in the claims, a "fluid" comprises liquid and/or gas, for example, a liquid-gas mixture that is predominantly liquid, such as a liquid with gas bubbles.

Suction cleaning system component 100 comprises a cleaning catheter 110 and a manifold 120. Cleaning catheter 110 comprises an elongate tube 20 and an expandable element 30, which is mounted to elongate tube 20 near a distal end of the elongate tube, and is expandable into contact with an inner surface of tracheal ventilation tube 160. For some applications, expandable element 30 comprises an inflatable element, such as an inflatable balloon, which is configured to expand upon being inflated. For these applications, the above-mentioned inflation source (e.g., a conventional syringe) is used to expand expandable element 30 by inflating the inflatable element, e.g., the balloon.

For other applications, expandable element 30 expands other than by inflation; for example, expandable element 30 may comprise a deformable element such as a gel, a foam, a fluid compartment, or a wire mesh or braid, which can be deformed to expand its width in the direction perpendicular to the main body longitudinal axis, either with or without an overall change in volume.

For some applications, expandable element 30 is mounted to elongate tube 20 at a site along a distal-most portion of the elongate tube, which distal-most portion has a length equal to 30% of a total length of elongate tube 20. Alternatively or additionally, for some applications, expandable element 30 is mounted to elongate tube 20 at a site within 20 mm of a distal end 21 of the elongate tube.

For some applications, expandable element 30 has a greatest outer diameter of at least 6 mm, no more than 12 mm, and/or between 6 and 12 mm when fully expanded (e.g., inflated) and unconstrained (i.e., not constrained by the tracheal ventilation tube or anything else), which is typically slightly greater than an inner diameter of tracheal ventilation tube 160, in order to provide good contact with the inner surface of the tracheal ventilation tube. For some applications, elongate tube 20 has an outer diameter of at least 6 mm, no more than 12 mm, and/or between 6 and 12 mm. For some applications, the greatest outer diameter of expandable element 30 when fully expanded (e.g., inflated) and unconstrained (i.e., not constrained by the tracheal ventilation tube or anything else) equals at least 60%, no more than 120%, and/or between 60% and 120% of the outer diameter of elongate tube 20.

Manifold 120 is shaped so as to define:
- a tubular chamber 122, which is shaped so as to allow passage therethrough of cleaning catheter 110, and which has an inlet 123 for the cleaning catheter at a proximal end 124 of tubular chamber 122; for some applications, tubular chamber 122 comprises a sealing element 46 that provides a fluid-tight seal between the outer surface of elongate tube 20 and the inner surface of tubular chamber 122;
- a ventilator port 60 in a lateral wall of tubular chamber 122; ventilator port 60 is configured to be coupled in fluid communication with the ventilator; and
- a tracheal ventilation tube port 55, which is configured to be coupled in fluid communication with a proximal end of tracheal ventilation tube 160.

Manifold 120 comprises an obstruction element 180, which is moveable with respect to (i) ventilator port 60 and (ii) expandable element 30. Obstruction element 180 is configured to assume a plurality of states, including an obstruction state, as shown in FIGS. 1A and 1B. In the obstruction state, obstruction element 180, at least during proximal withdrawal of expandable element 30 past ventilator port 60 while expandable element 30 is expanded, inhibits air flow between ventilator port 60 and at least a portion 126 of a proximally-facing external surface of expandable element 30.

Suction cleaning system component 100 is used clean an interior of tracheal ventilation tube 160 when suction cleaning system component 100 is connected to tracheal ventilation tube 160 and the ventilator. Typically, suction cleaning system component 100 is used in a closed endotracheal suction system environment.

During use, cleaning catheter 110 is first advanced distally through tubular chamber 122, and then through tracheal ventilation tube 160 to or slightly beyond the distal end of the tracheal ventilation tube. During this distal advancement, expandable element 30 is in a non-expanded state (i.e., not in full contact with the circumference of the inner surface of tracheal ventilation tube 160). For cleaning operation, expandable element 30 is then expanded, which induces contact between a portion of the outer surface of expandable element 30 and the inner surface of tracheal ventilation tube 160. While thus expanded, expandable element 30 is then withdrawn proximally through tracheal ventilation tube 160, such that the portion of the outer surface of expandable element 30 wipes the inner wall of tracheal ventilation tube 160. Typically, during this proximal withdrawal, suction is applied by the suction source via one or more distal suction orifices 25 of cleaning catheter 110, in order to remove the debris (which typically includes bacterial biofilm) wiped off of the inner wall of the tracheal ventilation tube by the expandable element. The one or more distal suction orifices 25 are disposed proximally to expandable element 30, and are in fluid connection with the suction source via elongate tube 20. For some applications, obstruction element 180 is shaped so as to define at least one lateral opening 182 having a cross-sectional area of between 1 mm2 and 25 mm2.

Lateral opening 182 allows passage of some air from the ventilator into tracheal ventilation tube 160 to assist the suction air flow of the cleaning catheter suction operation.

Before the proximal withdrawal of expandable element 30 past ventilator port 60, obstruction element 180 is positioned in the obstruction state, as shown in FIGS. 1A and 1B. During proximal withdrawal of expandable element 30 past ventilator port 60 while expandable element 30 is expanded, obstruction element 180 inhibits air flow between ventilator port 60 and the at least a portion 126 of the proximally-facing external surface of expandable element 30. In the absence of obstruction element 180, the air pressure from ventilator port 60 might dislodge debris from the at least a portion 126 of the proximally-facing external surface of expandable element 30 during the proximal withdrawal of expandable element 30 past ventilator port 60, and propel the debris distally around expandable element, through tracheal ventilation tube 160, and into the patient's lungs. As shown in FIG. 1C, after expandable element 30 has been withdrawn proximally beyond ventilator port 60, obstruction element 180 is moved out of the obstruction state, such as into the open state described hereinbelow with reference to FIG. 1C.

For some applications, obstruction element 180 is transitioned between at least a portion of the plurality of states manually by an operator of suction cleaning system component 100. For example, manifold 120 may comprise a user-control element, such as a sliding or rotating user handle coupled to obstruction element 180 through the wall of tubular chamber 122. For other applications, obstruction element 180 automatically transitions between at least a portion of the plurality of states. For example, distal advancement of elongate tube 20 may automatically transition the obstruction element to the obstruction state, and/or proximal withdrawal of elongate tube 20 may automatically transition the obstruction element out of the obstruction state.

For some applications, manifold 120 is configured such that the plurality of states further includes an air-flow state, in which obstruction element 180, at least when expandable element 30 is disposed distally to ventilator port 60 while expandable element 30 is expanded, allows air flow between ventilator port 60 and the at least a portion 126 of the proximally-facing external surface of expandable element 30 at a greater level than when obstruction element 180 is in the obstruction state. This air-flow state is not shown in FIGS. 1-C. For applications in which it occurs, this state occurs while expandable element 30 is disposed distally to ventilator port 60 while expanded, such as shown in FIG. 1A, and obstruction element 180 is positioned proximal to ventilator port 60. For some applications, obstruction element 180, when in the air-flow state, is configured to allow the air flow between ventilator port 60 and the at least a portion 126 of the proximally-facing external surface of expandable element 30 at at least twice, e.g., at least 5 times (such as at least 10 times), the level occurring when obstruction element 180 is in the obstruction state.

For concreteness, the level of air flow inhibition associated with different obstruction states of obstruction element 180 may be evaluated, for example, as the change dR of resistance "R" to flow $$R = P/F$$

where P is the ventilator pressure, in an experiment measuring the air flow "F" through tracheal ventilation tube port 55 when it is open to room environment and expandable element 30 not expanded and is situated between ventilator port 60 and tracheal ventilation tube port 55. Such an experiment can, for example, be realized using a conventional ventilator machine which measures both the pressure and flow rate provided. The ventilator is connected to ventilator port 60, while the ventilation port 55 is unconnected and open to the room air (i.e., open to atmospheric room pressure). The change dR is then the difference between the measured resistances R at different states of obstruction element 180.

For other applications, this air-flow state does not occur during use of suction cleaning system component 100, such as in applications in which the distal advancement of elongate tube 20 may automatically transition the obstruction element to the obstruction state, or in which the obstruction element is transitioned to the obstruction state before expansion of expandable element 30.

For some applications, manifold 120 is configured such that obstruction element 180, when in the obstruction state, inhibits air flow between ventilator port 60 and tubular chamber 122, such as shown in FIGS. 1A and 1B.

For some applications, manifold 120 is configured such that the plurality of states further includes an open state, such as shown in FIG. 1C. In this open state, obstruction element 180 allows air flow between ventilator port 60 and tracheal ventilation tube 160 via tubular chamber 122, at least when expandable element 30 is disposed proximally to ventilator port 60, such as shown in FIG. 1C. Expandable element 30 is optionally partially or completely unexpanded (e.g., deflated) in the state shown in FIG. 1C (as well as in FIGS. 3C, 4C, 5C, and 6C).

For some applications, a substantially impermeable and/or pliable sleeve 40 is provided for protecting an outer surface of cleaning catheter 110 that is positioned proximally beyond and outside of manifold 120. Sleeve 40 is sealed to inlet 123 of manifold 120.

For some applications, manifold 120 comprises a lavage port 184, as is known in the art.

Figures 2A, 2B:
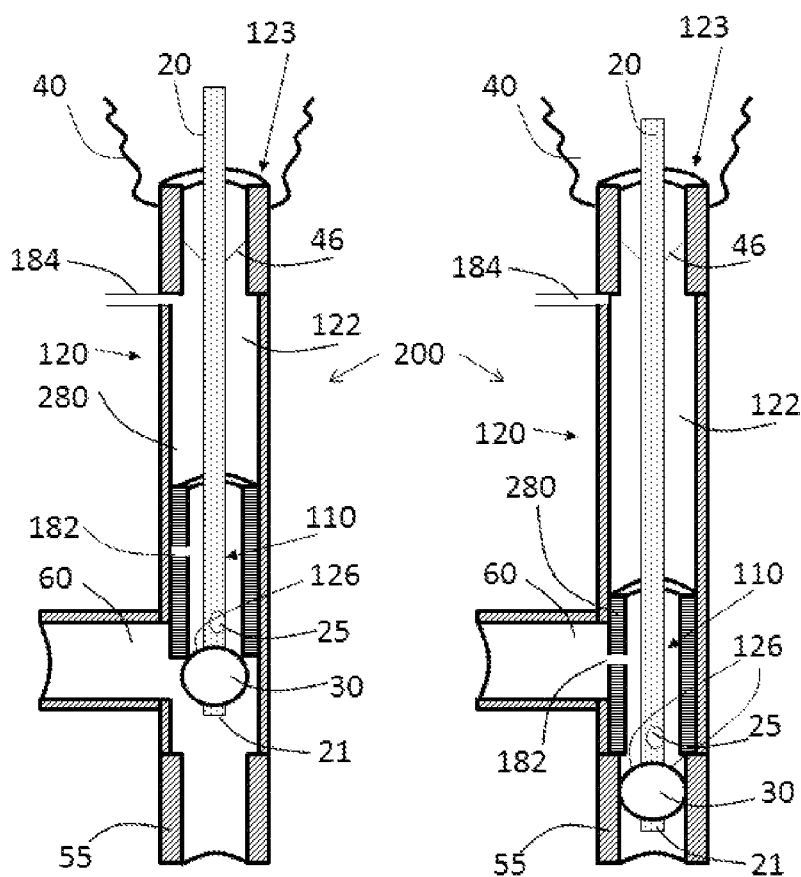
FIGS. 2A-C are schematic illustrations of another suction cleaning system component, in accordance with an application of the present invention.
Figure 2C:
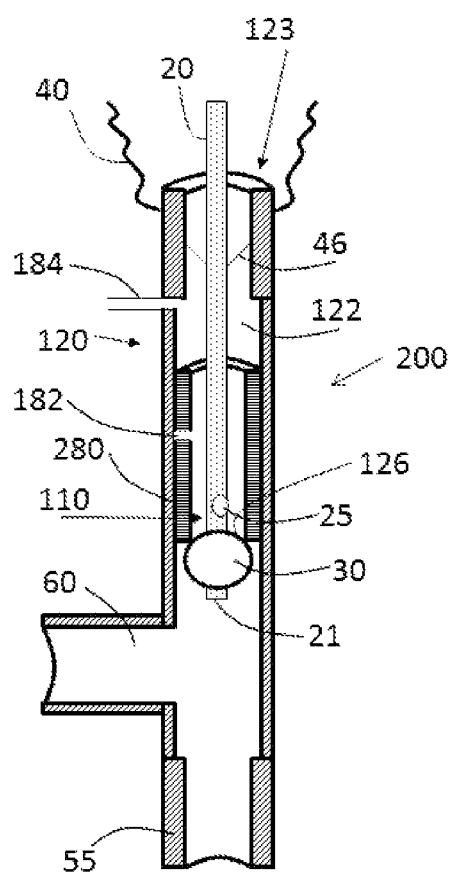
Figure 3C:
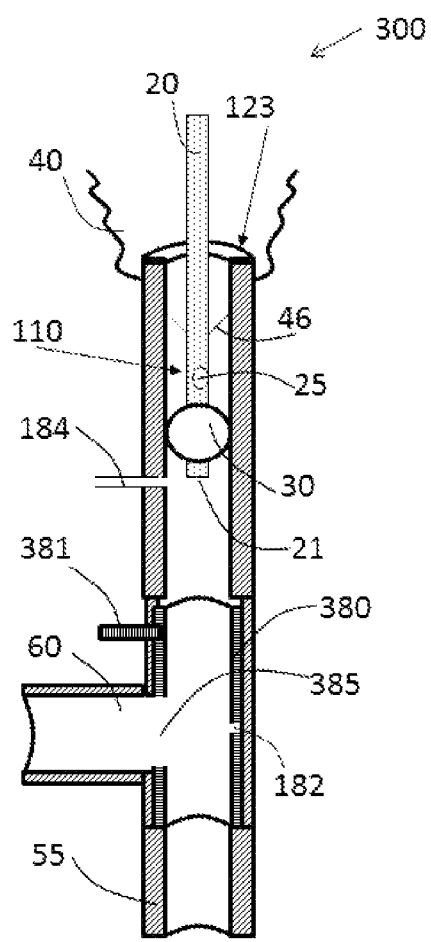
Figure 4C:
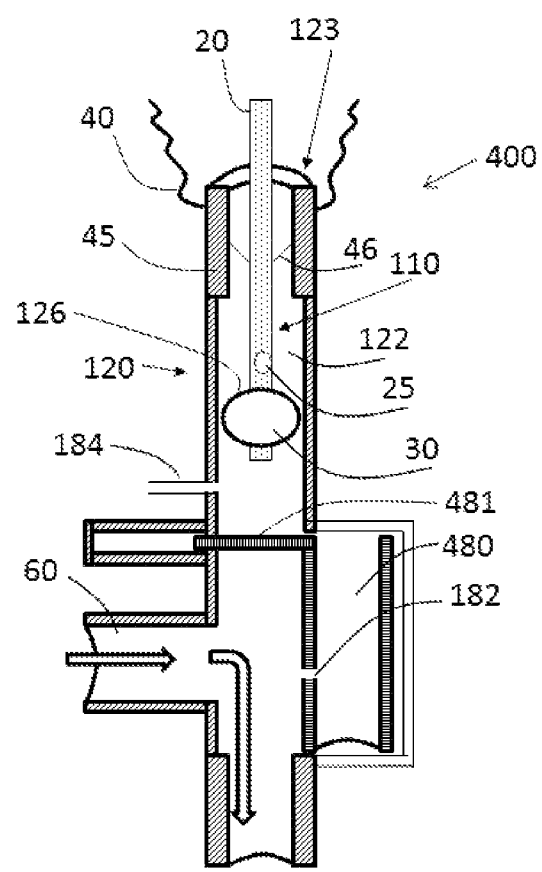

Reference is still made to FIGS. 1A-C, and is additionally made to FIGS. 2A-C, 3A-C, and 4A-C. FIGS. 2A-C are schematic illustrations of a suction cleaning system component 200, in accordance with an application of the present invention. FIGS. 3A-C are schematic illustrations of a suction cleaning system component 300, in accordance with an application of the present invention. FIGS. 4A-C are schematic illustrations of a suction cleaning system component 400, in accordance with an application of the present invention. Except as described below, suction cleaning system components 200, 300, and 400 are generally similar to suction cleaning system component 100, described hereinabove with reference to FIGS. 1A-C, and may incorporate any of the features of suction cleaning system component 100, mutatis mutandis. Like reference numerals refer to like elements. Suction cleaning system components 200, 300, and 400 comprise an obstruction element 280, an obstruction element 380, and an obstruction element 480, respectively, rather than obstruction element 180 of suction cleaning system component 100.

Each of obstruction elements 180, 280, 380, and 480 comprises an open-ended tube having a longitudinal axis parallel to a longitudinal axis of tubular chamber 122. For some applications, the longitudinal axis of the open-ended tube is coaxial with the longitudinal axis of tubular chamber 122, such as shown in FIGS. 1A-C, 2A-C, and 3A-C.

For some applications, the open-ended tube is disposed within the tubular chamber, such as shown in FIGS. 1A-C, 2A-C, and 3A-C; for some of these applications, the open-ended tube is longitudinally-slidably disposed within the tubular chamber, such as shown in FIGS. 1A-C and 2A-C.

For some applications, manifold 120 comprises a user-control element, such as a sliding or rotating user handle coupled to obstruction element 180 through the wall of tubular chamber 122. The user-control element is fixed to the open-ended tube and extends outside of tubular chamber 122, and is configured to longitudinally slide the open-ended tube within the tubular chamber.

Reference is again made to FIGS. 1A-C. For some applications, tracheal ventilation tube port 55 has a first inner perimeter and a longitudinal axis parallel to the longitudinal axis of the open-ended tube, and the open-ended tube has a second inner perimeter which is more than 90% of the first inner perimeter. As a result, expandable element 30 slides into the open-ended tube during the proximal withdrawal of expandable element 30 while expandable element 30 is expanded.

Reference is made to FIGS. 2A-C. For some applications, manifold 120 is configured such that the proximal withdrawal of expandable element 30, while expandable element 30 is expanded, automatically transitions obstruction element 280 out of the obstruction state.

For some applications, manifold 120 is configured such that the plurality of states further includes an open state, in which obstruction element 280 allows air flow between ventilator port 60 and tracheal ventilation tube 160 via the tubular chamber, at least when expandable element 30 is disposed proximally to ventilator port 60, such as shown in FIG. 2C. Proximal withdrawal of expandable element 30, while expandable element 30 is expanded, automatically transitions obstruction element 280 out of the obstruction state into the open state. For some applications, manifold 120 is configured such that obstruction element 280, when in the obstruction state in at least some longitudinal positions with respect to ventilator port 60, is also in a partially-open state, such as shown in FIG. 2B. In this partially-open state, obstruction element 280 allows a lower level of the air flow between ventilator port 60 and tracheal ventilation tube 160 than when obstruction element 280 is in the open state. (When in other longitudinal positions with respect to ventilator port 60, obstruction element 280 is not necessarily in the partially-open state. For example, obstruction element 280 is not in the partially-open state when expandable element 30 is proximally withdrawn slightly from the position shown in FIG. 2A, such that the expandable element comes in contact with the distal end of obstruction element 280 but is still distal to ventilator port 60.)

Reference is still made to FIGS. 2A-C. For some applications, tracheal ventilation tube port 55 has a first inner perimeter (e.g., diameter) and a longitudinal axis parallel to the longitudinal axis of the open-ended tube, and the open-ended tube has a second inner perimeter (e.g., diameter) which is less than 90% of the first inner perimeter. As a result, the proximal withdrawal of expandable element 30, while the expandable element is expanded (typically, to the larger first inner perimeter (e.g., diameter) of tracheal ventilation tube port 55), pushes the open-ended tube proximally, thereby automatically transitioning obstruction element 280 out of the obstruction state. (Typically, the first inner perimeter (e.g., diameter) of tracheal ventilation tube port 55 is equal to, or approximately equal to, the inner perimeter (e.g., diameter) of tracheal ventilation tube 160.)

Reference is made to FIGS. 3A-C. For some applications, the open-ended tube is rotatably disposed within tubular chamber 122, and a wall of the open-ended tube is shaped so as to define a lateral fenestration 385, which, when obstruction element 380 is in the obstruction state, as shown in FIGS. 3A and 3B, is not rotationally aligned with ventilator port 60, so as to inhibit the air flow between ventilator port 60 and the at least a portion 126 of the proximally-facing external surface of the expandable element. For some applications, manifold 120 is configured such that the plurality of states further includes an open state, in which obstruction element 380 is rotationally aligned with ventilator port 60, so as to allow air flow between ventilator port 60 and tracheal ventilation tube 160 via the fenestration and the tubular chamber, at least when the expandable element is disposed proximally to ventilator port 60, such as shown in FIG. 3C.

For some applications, manifold 120 comprises a user-control handle 381, which is fixed to the open-ended tube and extends outside of tubular chamber 122, and is configured to rotate the open-ended tube within the tubular chamber.

Reference is now made to FIGS. 4A-C. For some applications, manifold 120 is shaped so as to define a lateral extension 489, at least a portion of which longitudinally overlaps ventilator port 60. Manifold 120 is configured such that when obstruction element 480 is in the obstruction state, the open-ended tube is coaxial with tracheal ventilation tube port 55, such as shown in FIGS. 4A and 4B. For some applications, manifold 120 is configured such that the plurality of states further includes an open state, in which the open-ended tube is non-coaxial with tracheal ventilation tube port 55, and is disposed at least partially within lateral extension 489, so as to allow air flow between ventilator port 60 and tracheal ventilation tube 160, at least when the expandable element is disposed proximally to ventilator port 60, such as shown in FIG. 4C. For some applications, manifold 120 comprises a user-control handle 481, which is fixed to the open-ended tube and extends outside of tubular chamber 122, and is configured to laterally move the open-ended tube into and out of lateral extension 489.

Figures 5A, 5B:
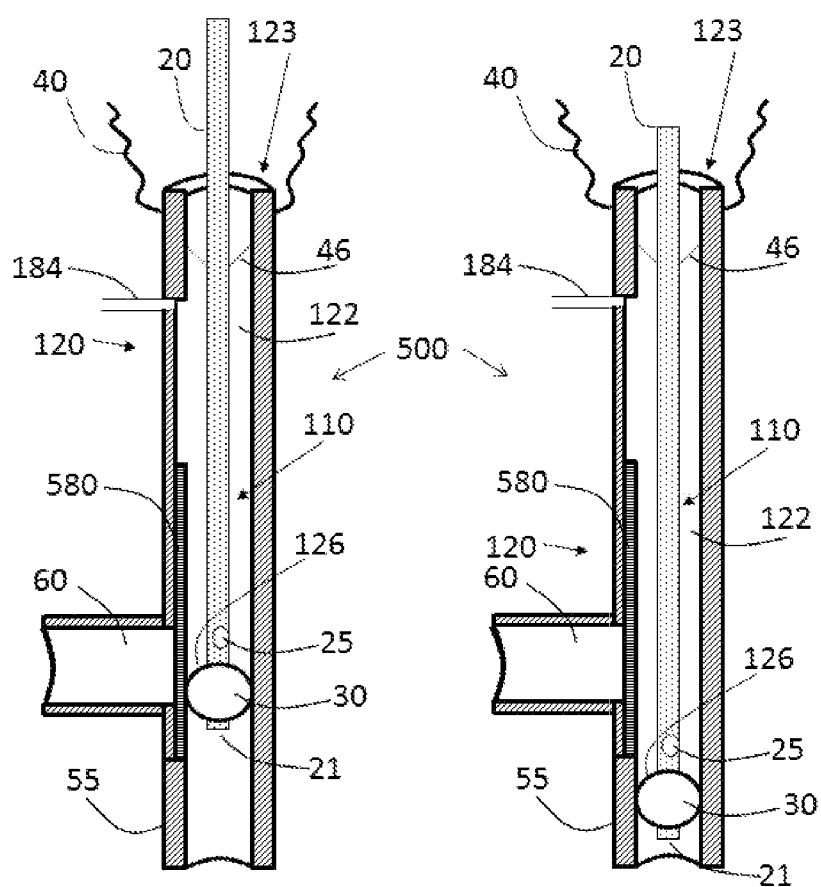
FIGS. 5A-C are schematic illustrations of another suction cleaning system component, in accordance with an application of the present invention.
Figure 5C:
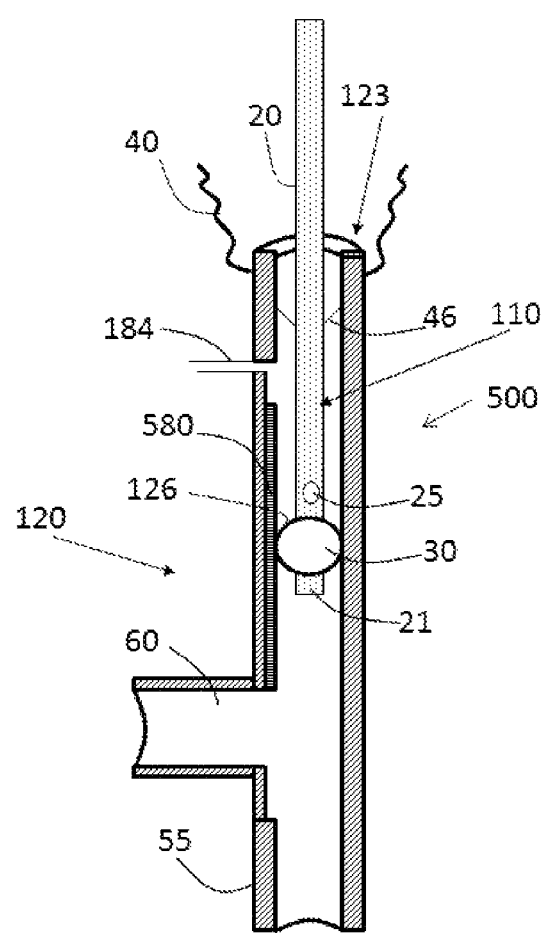

Reference is now made to FIGS. 5A-C, which are schematic illustrations of a suction cleaning system component 500, in accordance with an application of the present invention. Except as described below, suction cleaning system component 500 is generally similar to suction cleaning system components 100, 200, and 300, described hereinabove with reference to FIGS. 1A-C, 2A-C, and 3A-C, respectively, and may incorporate any of the features of suction cleaning system components 100, 200, and/or 300, mutatis mutandis. Like reference numerals refer to like elements. Suction cleaning system component 500 comprises an obstruction element 580, rather than obstruction element 180 of suction cleaning system component 100.

Obstruction element 580 comprises an arcuate portion (i.e., less than a complete circle) of a cylindrical tube having a longitudinal axis parallel to a longitudinal axis of tubular chamber 122. For some applications, the arcuate portion is longitudinally-slidably disposed within tubular chamber 122, as shown in FIGS. 5A-C. For other applications, the arcuate portion is rotatably disposed within tubular chamber 122, similar to the configuration described hereinabove with reference to FIGS. 3A-C (configuration not shown). For some applications, manifold 120 comprises a user-control handle, which is fixed to the arcuate portion and extends outside of the tubular chamber, and is configured to longitudinally slide the arcuate portion within the tubular chamber.

Figures 6A, 6B:
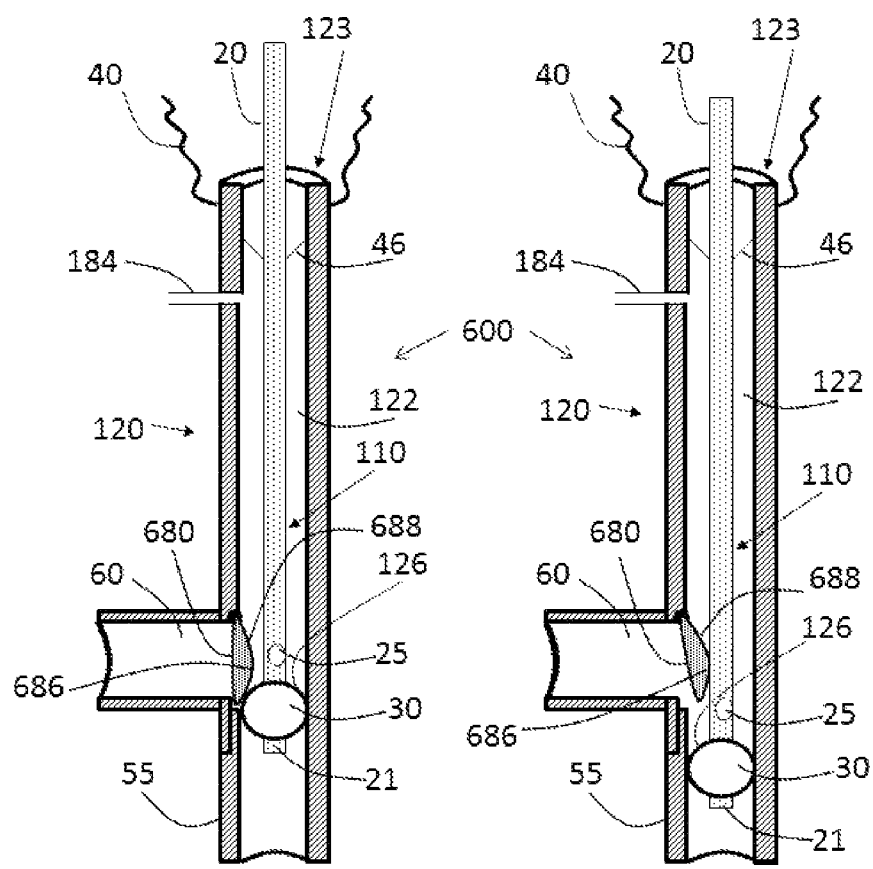
FIGS. 6A-C are schematic illustrations of yet another suction cleaning system component, in accordance with an application of the present invention.
Figure 6C:
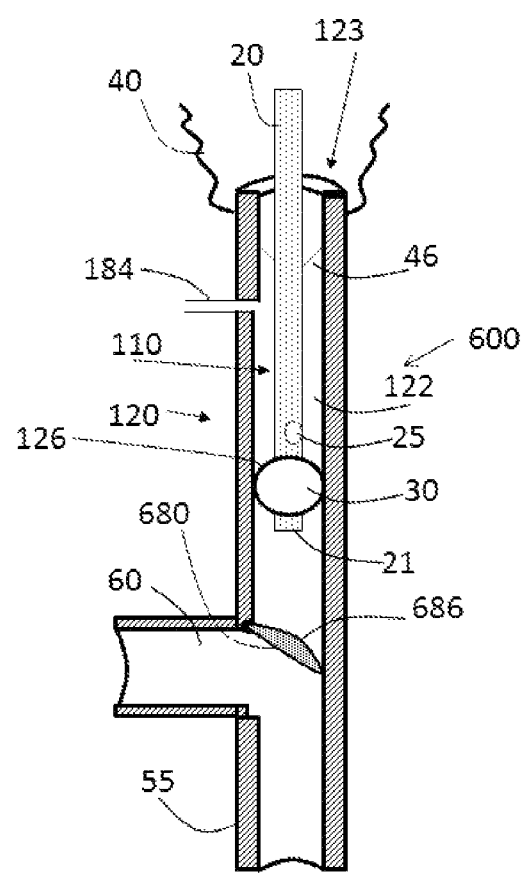

Reference is now made to FIGS. 6A-C, which are schematic illustrations of a suction cleaning system component 600, in accordance with an application of the present invention. Except as described below, suction cleaning system component 600 is generally similar to suction cleaning system component 100, described hereinabove with reference to FIGS. 1A-C. Suction cleaning system component 600 may incorporate any of the features of suction cleaning system components 100, 200, 300, 400, and/or 500 mutatis mutandis. Like reference numerals refer to like elements. Suction cleaning system component 600 comprises an obstruction element 680, rather than obstruction element 180 of suction cleaning system component 100. In this configuration, manifold 120 is configured such that at least one site of obstruction element 680 is longitudinally fixed with respect to tubular chamber 122.

Obstruction element 680 comprises a flap 686, which is disposed within tubular chamber 122 and is attached to the lateral wall of tubular chamber 122, for example at or proximal to a proximal end of ventilator port 60. Manifold 120 is configured such that when flap 686 is in the obstruction state, flap 686 covers ventilator port 60 (not necessarily with a fluid-tight seal) and inhibits air flow between ventilator port 60 and the at least a portion 126 of the proximally-facing external surface of expandable element 30. Flap 686 may be integrally formed with the lateral wall of tubular chamber 122, or may comprise a separate element that is fixed to the lateral wall during manufacture. The capability of the flap to flap, or swing, with respect to ventilator port 60 may be provided by the flexibility of the material of the flap, and/or by an optional joint (optionally comprising a hinge axis) that fixes the flap to the lateral wall. For some applications, the flap comprises a flexible material, such as silicone, PVC, polyurethane, or other polymers.

For some applications, flap 686 is elastically biased to an open configuration in which flap 686 does not cover ventilator port 60, such as shown in FIG. 6C. For some applications, flap 686 is configured to assume a partially-open state, such as shown in FIG. 6A, in which state flap 686 allows a lower level of the air flow between ventilator port 60 and the at least a portion 126 of the proximally-facing external surface of the expandable element than when flap 686 in the open configuration, such as shown in FIG. 6C. For some applications, flap 686 is configured to automatically assume the partially-open state when expandable element 30 is disposed at a longitudinal position distal to ventilator port 60, such as shown in FIG. 6C. For some applications, flap 686 is configured to automatically assume the partially-open state or the open configuration when expandable element 30 is disposed at a longitudinal position distal to ventilator port 60. For some applications, such as shown in FIG. 6A, elongate tube 20 of cleaning catheter 110 is configured to hold flap 686 in the partially-open state, and prevents flap 686 from assuming the open configuration.

For some applications, manifold 120 is configured such that the proximal withdrawal of expandable element 30 fully over and proximally beyond flap 686, while expandable element 30 is expanded, automatically transitions flap 686 out of the obstruction state.

For some applications, manifold 120 is configured such that the proximal withdrawal of expandable element 30, while expandable element 30 is expanded, automatically transitions flap 686 to the obstruction state, by expandable element 30 pushing flap 686 against ventilator port 60.

For some applications, flap 686 is elastically biased to an open configuration in which flap 686 does not cover ventilator port 60. For some of these applications, manifold 120 is configured such that the proximal withdrawal of expandable element 30 fully over and proximally beyond flap 686, while the expandable element is expanded, allows flap 686 to assume the open configuration. Alternatively or additionally, for some of these applications, the proximal withdrawal of expandable element 30 to a first longitudinal position, while expandable element 30 is expanded, automatically transitions flap 686 to the obstruction state, and manifold 120 is configured such that the proximal withdrawal of expandable element 30 to a second longitudinal position, while expandable element 30 is expanded, allows flap 686 to assume the open configuration, the second longitudinal position being proximal to the first longitudinal position.

For some applications, flap 686 is shaped such that a surface 688 of flap 686 facing radially inwardly, when flap 686 is in the obstruction state, is convex toward a central longitudinal axis of tubular chamber 122. Alternatively or additionally, for some applications, flap 686 is shaped such that a distal portion of flap 686, when flap 686 is in the obstruction state, is tapered toward a distal end of flap 686. As a result of either of these configurations, the proximal withdrawal of expandable element 30, while expanded, causes the expandable element to contact the convex surface and push the flap radially outward against ventilator port 60.

The scope of the present invention includes embodiments described in the following applications, which are incorporated herein by reference. In an embodiment, techniques and apparatus described in one or more of the following applications are combined with techniques and apparatus described herein. In case of conflict between the definitions used herein and those used in the following applications, the definitions used herein shall control.

PCT Publication WO/2012/131626 to Einav et al.;
PCT Publication WO 2013/030821 to Zachar et al.;
UK Publication GB 2482618 A to Einav et al.;
UK Application GB 1119794.4, filed Nov. 16, 2011;
U.S. Provisional Application 61/468,990, filed Mar. 29, 2011;
U.S. Provisional Application 61/473,790, filed Apr. 10, 2011;
U.S. Provisional Application 61/483,699, filed May 8, 2011;
U.S. Provisional Application 61/496,019, filed Jun. 12, 2011;
U.S. Provisional Application 61/527,658, filed Aug. 26, 2011;
U.S. Provisional Application 61/539,998, filed Sep. 28, 2011;
U.S. Provisional Application 61/560,385, filed Nov. 16, 2011;
U.S. Provisional Application 61/603,340, filed Feb. 26, 2012;
U.S. Provisional Application 61/603,344, filed Feb. 26, 2012;
U.S. Provisional Application 61/609,763, filed Mar. 12, 2012;
U.S. Provisional Application 61/613,408, filed Mar. 20, 2012;
U.S. Provisional Application 61/635,360, filed Apr. 19, 2012;
U.S. Provisional Application 61/655,801, filed Jun. 5, 2012;
U.S. Provisional Application 61/660,832, filed Jun. 18, 2012; and
U.S. Provisional Application 61/673,744, filed Jul. 20, 2012.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a tracheal ventilation tube and a ventilator, the apparatus comprising:
    a cleaning catheter, which comprises an elongate tube and an expandable element, which is mounted to the elongate tube, and is expandable into contact with an inner surface of the tracheal ventilation tube; and a manifold, which:
        is shaped so as to define (a) a tubular chamber, which is shaped so as to allow passage therethrough of the cleaning catheter, and which has an inlet for the cleaning catheter at a proximal end of the tubular chamber, (b) a ventilator port in a lateral wall of the tubular chamber, which ventilator port is configured to be coupled in fluid communication with the ventilator, and (c) a tracheal ventilation tube port, which is configured to be coupled in fluid communication with a proximal end of the tracheal ventilation tube, and
        comprises an obstruction element, which is (a) moveable with respect to (i) the ventilator port and (ii) the expandable element, and (b) configured to assume a plurality of states, including an obstruction state, in which state the obstruction element, at least during proximal withdrawal of the expandable element directly across the ventilator port while the expandable element is expanded, inhibits air flow between the ventilator port and at least a portion of a proximally-facing external surface of the expandable element.

2. The apparatus according to claim 1, wherein the manifold is configured such that the obstruction element, when in the obstruction state, inhibits air flow between the ventilator port and the tubular chamber.

3. The apparatus according to claim 1, wherein the expandable element comprises an inflatable element.

4. The apparatus according to claim 3, wherein the inflatable element comprises an inflatable balloon.

5. The apparatus according to claim 1, wherein the expandable element is mounted to the elongate tube at a site along a distal-most portion of the elongate tube, which distal-most portion has a length equal to 30% of a total length of the elongate tube.

6. The apparatus according to claim 1, wherein the expandable element is mounted to the elongate tube at a site within 20 mm of a distal end of the elongate tube.

7. The apparatus according to claim 1, for use with a suction source, wherein a distal portion of the cleaning catheter comprises one or more distal suction orifices, which are disposed proximally to the expandable element, and which are in fluid connection with the suction source.

8. The apparatus according to claim 1, wherein the obstruction element is shaped so as to define a lateral opening having a cross-sectional area of between 1 mm2 and 25 mm2.

9. The apparatus according to claim 1, wherein the manifold is configured such that the plurality of states further includes an air-flow state, in which state the obstruction element, at least when the expandable element is disposed distally to the ventilator port while the expandable element is expanded, allows air flow between the ventilator port and the at least a portion of the proximal surface of the expandable element at a greater level than when the obstruction element is in the obstruction state.

10. The apparatus according to claim 9, wherein the obstruction element, when in the air-flow state, is configured to allow the air flow between the ventilator port and the at least a portion of the proximal surface of the expandable element at at least twice the level occurring when the obstruction element is in the obstruction state.

11. The apparatus according to claim 10, wherein the obstruction element, when in the air-flow, is configured to allow the air flow between the ventilator port and the at least a portion of the proximal surface of the expandable element at at least 5 times the level occurring when the obstruction element is in the obstruction state.

12. The apparatus according to claim 1, wherein the manifold is configured such that the plurality of states further includes an open state, in which state the obstruction element allows air flow between the ventilator port and the tracheal ventilation tube via the tubular chamber, at least when the expandable element is disposed proximally to the ventilator port.

13. The apparatus according to claim 12, wherein the manifold is configured such that the plurality of states further includes a partially-open state, in which state the obstruction element allows a lower level of the air flow between the ventilator port and the tracheal ventilation tube than when the obstruction element is in the open state.

14. Apparatus for use with a tracheal ventilation tube and a ventilator, the apparatus comprising:
    a cleaning catheter, which comprises an elongate tube and an expandable element, which is mounted to the elongate tube, and is expandable into contact with an inner surface of the tracheal ventilation tube; and a manifold, which:
        is shaped so as to define (a) a tubular chamber, which is shaped so as to allow passage therethrough of the cleaning catheter, and which has an inlet for the cleaning catheter at a proximal end of the tubular chamber, (b) a ventilator port in a lateral wall of the tubular chamber, which ventilator port is configured to be coupled in fluid communication with the ventilator, and (c) a tracheal ventilation tube port, which is configured to be coupled in fluid communication with a proximal end of the tracheal ventilation tube, and
        comprises an obstruction element, which is (a) moveable with respect to (i) the ventilator port and (ii) the expandable element, and (b) configured to assume a plurality of states, including an obstruction state, in which state the obstruction element, at least during proximal withdrawal of the expandable element past the ventilator port while the expandable element is expanded, inhibits air flow between the ventilator port and at least a portion of a proximally-facing external surface of the expandable element; and
        wherein the manifold is configured such that the proximal withdrawal of the expandable element, while the expandable element is expanded, automatically transitions the obstruction element out of the obstruction state.

15. The apparatus according to claim 14, wherein the manifold is configured such that:
    the plurality of states further includes an open state, in which state the obstruction element allows air flow between the ventilator port and the tracheal ventilation tube via the tubular chamber, at least when the expandable element is disposed proximally to the ventilator port, and the proximal withdrawal of the expandable element, while the expandable element is expanded, automatically transitions the obstruction element out of the obstruction state into the open state.

16. The apparatus according to claim 1, wherein the manifold is configured such that at least one site of the obstruction element is longitudinally fixed with respect to the tubular chamber.

17. Apparatus for use with a tracheal ventilation tube and a ventilator, the apparatus comprising:
  a cleaning catheter, which comprises an elongate tube and an expandable element, which is mounted to the elongate tube, and is expandable into contact with an inner surface of the tracheal ventilation tube; and a manifold, which:
    is shaped so as to define (a) a tubular chamber, which is shaped so as to allow passage therethrough of the cleaning catheter, and which has an inlet for the cleaning catheter at a proximal end of the tubular chamber, (b) a ventilator port in a lateral wall of the tubular chamber, which ventilator port is configured to be coupled in fluid communication with the ventilator, and (c) a tracheal ventilation tube port, which is configured to be coupled in fluid communication with a proximal end of the tracheal ventilation tube, and
    comprises an obstruction element, which is (a) moveable with respect to (i) the ventilator port and (ii) the expandable element, and (b) configured to assume a plurality of states, including an obstruction state, in which state the obstruction element, at least during proximal withdrawal of the expandable element past the ventilator port while the expandable element is expanded, inhibits air flow between the ventilator port and at least a portion of a proximally-facing external surface of the expandable element; and
    wherein the obstruction element comprises a flap, which is disposed within the tubular chamber and is attached to the lateral wall of the tubular chamber, and
    wherein the manifold is configured such that when the flap is in the obstruction state, the flap covers the ventilator port and inhibits air flow between the ventilator port and the at least a portion of the proximally-facing external surface of the expandable element.

18. The apparatus according to claim 17, wherein the flap is attached to the lateral wall at or proximal to a proximal end of the ventilator port.

19. Apparatus for use with a tracheal ventilation tube and a ventilator, the apparatus comprising:
  a cleaning catheter, which comprises an elongate tube and an expandable element, which is mounted to the elongate tube, and is expandable into contact with an inner surface of the tracheal ventilation tube; and a manifold, which:
    is shaped so as to define (a) a tubular chamber, which is shaped so to allow passage therethrough of the cleaning catheter, and which has an inlet for the cleaning catheter at a proximal end of the tubular chamber, (b) a ventilator port in a lateral wall of the tubular chamber, which ventilator port is configured to be coupled in fluid communication with the ventilator, and (c) a tracheal ventilation tube port, which is configured to be coupled in fluid communication with a proximal end of the tracheal ventilation tube, and
    comprises a flap which is (a) disposed within the tubular chamber, (b) attached to the lateral wall of the tubular chamber, and (c) configured to assume a plurality of states, including an obstruction state, in which state the flap covers the ventilator port and inhibits air flow between the ventilator port and at least a portion of a proximally-facing external surface of the expandable element.

* * * * *